United States Patent
Becker et al.

(10) Patent No.: US 11,478,531 B2
(45) Date of Patent: Oct. 25, 2022

(54) COMPOSITIONS AND METHODS FOR INDUCING A TREG PHENOTYPE AND METHODS FOR USE FOR THE SAME

(71) Applicant: UNIVERSITY OF SOUTH CAROLINA, Columbia, SC (US)

(72) Inventors: William Becker, Columbia, SC (US); Prakash Nagarkatti, Columbia, SC (US); Mitzi Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 77 days.

(21) Appl. No.: 16/717,340

(22) Filed: Dec. 17, 2019

(65) Prior Publication Data

US 2020/0268848 A1   Aug. 27, 2020

Related U.S. Application Data

(60) Provisional application No. 62/808,403, filed on Feb. 21, 2019.

(51) Int. Cl.
| | |
|---|---|
| *A61K 38/18* | (2006.01) |
| *A61K 31/7105* | (2006.01) |
| *A61P 29/00* | (2006.01) |
| *C07K 16/28* | (2006.01) |
| *C12N 15/113* | (2010.01) |
| *A61K 47/68* | (2017.01) |

(52) U.S. Cl.
CPC ...... *A61K 38/1841* (2013.01); *A61K 31/7105* (2013.01); *A61K 47/6873* (2017.08); *A61P 29/00* (2018.01); *C07K 16/2809* (2013.01); *C07K 16/2863* (2013.01); *C12N 15/113* (2013.01)

(58) Field of Classification Search
CPC . A61K 38/1841; A61P 29/00; C07K 16/2863; C07K 16/2809
See application file for complete search history.

(56) References Cited

PUBLICATIONS

Nishida, T., et al. Specific aqueous humor factors induce activation of regulatory T cells. Invest. Ophthalmol. Vis. Sci., 1999, 40: 2268-2274.*
ThermoFisher Scienfic Isting for anti-TGFbR3 antibodies, https://www.thermofisher.com/antibody/primary/query/Tgfbr3%20antibody, accessed on Apr. 20, 2021.*
Alvarez, et al. "TGFβ2 mediates the effects of Hedgehog on hypertrophic differentiation and PTHrP expression" *Development* 129 (2002) pp. 1913-1924.
Baumjohann, et al. "MicroRNA-mediated regulation of T helper cell differentiation and plasticity" *Nat. Rev. Immun.* 13 (2013) pp. 666-678.
Campos-Mora, et al. "Neuropilin-1 in transplantation tolerance" *Front. Immun.* 4:405 (2013) pp. 1-9.
Chen, et al. "Development of thymic Foxp3+ regulatory T cells: TGF-β matters" *Eur. J. Immun.* 45 (2015) pp. 958-965.
Chen, et al. "Conversion of peripheral CD4+CD25− naive T cells to CD4+CD25+ regulatory T cells by TGF-β induction of transcription factor Foxp3" *J. Exp. Med.* 198(12) (2003) pp. 1875-1886.
Daley, et al. "A key role for TGF-B signaling to T cells in the long-term acceptance of allografts" *J. Immun.* 179 (2007) pp. 3648-3654.
Daniel, et al. "Interferon-gamma producing regulatory T cells as a diagnostic and therapeutic tool in organ transplantation" *Int. Rev. Immun.* 33 (2014) pp. 195-211.
Desreumaux, et al. "Safety and efficacy of antigen-specific regulatory T-cell therapy for patients with refractory Crohn's disease" *Gastroenterology* 143 (2012) pp. 1207-1217.
Druz, et al. "A novel microRNA mmu-miR-466h affects apoptosis regulation in mammalian cells" *Biotech. Bioeng.* 108 (2011) pp. 1651-1661.
Edozie, et al. "Regulatory T-cell therapy in the induction of transplant tolerance: the issue of subpopulations" *Transplantation* 98 (2014) pp. 370-379.
Fontana, et al. "Loeys-Dietz syndrome type 4, caused by chromothripsis, involving the TGFB2 gene" *Gene* 538 (2014) pp. 69-73.
Francisco, et al. "PD-L1 regulates the development, maintenance, and function of induced regulatory T cells" *J. Exp. Med.* 206 (2009) pp. 3015-3029.
Gagliani, et al. "Coexpression of CD49b and LAG-3 identifies human and mouse T regulatory type 1 cells" *Nat. Med.* 19 (2013) pp. 739-746.
Gu, et al. "Requirements of transcription factor Smad-dependent and -independent TGF-β signaling to control discrete T-cell functions" *PNAS* 109 (2012) pp. 905-910.
Hu, et al. "MiR-21 controls in situ expansion of CCR6+ regulatory T cells through PTEN/AKT pathway in breast cancer" *Immun. Cell Biol.* 93 (2015) pp. 753-764.

(Continued)

*Primary Examiner* — Prema M Mertz
(74) *Attorney, Agent, or Firm* — Dority & Manning, P.A.

(57) ABSTRACT

The present application relates to induction of a Treg phenotype in mammalian naïve CD4+ T cells. In certain embodiments, the methods and compositions described can be applied as methods to treat autoimmune disorders or transplant complications (e.g., lupus and graft-versus-host disease) and may be used in combination with, but do not require, systemic immune suppression, such as a chemotherapeutic agent. In particular, embodiments of the disclosure can utilize transforming growth factor-beta 2 (TGFB2), molecules that stimulate the production of TGFB2, inhibitors of molecules that suppress production of TGFB2, or molecules that effect the function of TGFB2 to induce a Treg phenotype in naïve CD4+ T cells from a mammal. Provided herein are embodiments and examples demonstrating the production of Treg cells, as well as the application of Treg cells in modulating the inflammatory response present in certain diseases.

4 Claims, 31 Drawing Sheets
Specification includes a Sequence Listing.

(56) References Cited

PUBLICATIONS

Inoue, et al. "The rodent-specific microRNA cluster within the Sfmbt2 gene is imprinted and essential for placental development" *Cell Rep.* 19 (2017) pp. 949-956.
Kuzmin, et al. "The PcG gene Sfmbt2 is paternally expressed in extraembryonic tissues" *Gene Exp. Patt.* 8 (2008) pp. 107-116.
Langer, et al. "Quantitative trait analysis reveals transforming growth factor-β2 a positive regulator of early hematopoietic progenitor and stem cell function" *J. Exp. Med.* 199 (2004) pp. 5-14.
Leavy, O. "The PTEN stabilizer" *Nat. Rev. Immun.* 15 (2015) p. 71.
Li, et al. "MicroRNA-4661 inhibits antiviral innate immune response by targeting interferon-alpha" *Cell Mol. Immun.* 9 (2012) pp. 497-502.
Li, et al. "Transforming growth factor-β regulation of immune responses" *Ann. Rev. Immun.* 24 (2006) pp. 99-146.
Lindsay, et al. "Loss-of-function mutations in TGFB2 cause a syndromic presentation of thoracic aortic aneurysm" *Nat. Genet.* 44 (2012) pp. 922-927.
Liston, et al. "Dicer-dependent microRNA pathway safeguards regulatory T cell function" *J. Exp. Med.* 205 (2008) pp. 1993-2004.
Liu, et al. "A critical function for TGF-β signaling in the development of natural $CD4^{+CD25+Foxp3+}$ regulatory T cells" *Nat. Immun.* 9 (2008) pp. 632-640.
Lodish, et al. "Micromanagement of the immune system by microRNAs" *Nat. Rev. Immun.* 8 (2008) pp. 120-130.
Lu, et al. "Tumor suppressive microRNA-200a inhibits renal cell carcinoma development by directly targeting TGFB2" *Tumor Biol.* 36 (2015) pp. 6691-6700.
Lu, et al. "Function of miR-146a in controlling Treg cell-mediated regulation of Th1 responses" *Cell* 142 (2010) pp. 914-929.
Lu, et al. "Foxp3-dependent microRNA155 confers competitive fitness to regulatory T cells by targeting SOCS1 protein" *Immunity* 30 (2009) pp. 80-91.
Luo, et al. "Sfmbt2 10th intron-hosted miR-466(a/e)-3p are important epigenetic regulators of Nfat5 signaling, osmoregulation and urine concentration in mice" *Biochim. Biophys. Acta* 1839 (2014) pp. 97-106.
Ma, et al. "MicroRNA-4661 upregulates IL-10 expression in TLR-triggered macrophages by antagonizing RNA-binding protein tristetiaprolin-mediated IL-10 mRNA degradation" *J. Immun.* 184 (2010) pp. 6053-6059.
Marcen, D.R. "Immunosuppressive drugs in kidney transplantation" *Drugs* 69 (2012) pp. 2227-2243.
Martínez-Armenta, et al. "TGFβ2 regulates hypothalamic Trh expression through the TGFβ inducible early gene-1 (TIEG1) during fetal development" *Mol. Cell. Endocr.* 400, (2015) pp. 129-139.
Mellor, et al. "Physiologic control of the functional status of Foxp3+ regulatory T cells" *J Immun.* 186 (2011) pp. 4535-4540.
Mittelbrunn, et al. "Unidirectional transfer of microRNA-loaded exosomes from T cells to antigen-presenting cells" *Nat. Comm.* 2:282 (2011) pp. 1-10.
Morris, P.J. "Transplantation—a medical miracle of the 20th century" *N. Eng. J. Med.* 351 (2004) pp. 2678-2680.
Murugaiyan, et al. "MicroRNA-21 promotes Th17 differentiation and mediates experimental autoimmune encephalomyelitis" *J. Clin. Invest.* 125 (2015) pp. 1069-1080.
Namba, et al. "Induction of regulatory T cells by the immunomodulating cytokines α-melanocyte-stimulating hormone and transforming growth factor-β2" *J. Leukoc. Biol.* 72 (2002) pp. 946-952.
Niu, et al. "MicroRNA-153 inhibits osteosarcoma cells proliferation and invasion by targeting TGF-β2" *PLoS One* 10:e0119225 (2015) pp. 1-11.
O'Connell, et al. "MicroRNA regulation of inflammatory responses" *Ann. Rev. Immun.* 30 (2012) pp. 295-312.
Okoye, et al. "MicroRNA-containing T-regulatory-cell-derived exosomes suppress pathogenic T helper 1 cells" *Immunity* 41 (2014) pp. 89-103.
Parmar, et al. "Ex vivo fucosylation of third-party human regulatory T cells enhances anti-graft-versus-host disease potency in vivo" *Blood* 125 (2015) pp. 1502-1506.
Peterson, R.A. "Regulatory T-cells: diverse phenotypes integral to immune homeostasis and suppression" *Toxic. Path.* 40 (2012) pp. 186-204.
Redpath, et al. "ICOS controls Foxp3+ regulatory T-cell expansion, maintenance and IL-10 production during helminth infection" *Eur. J. Immun.* 43 (2013) pp. 705-715.
Regateiro, et al. "TGF-β in transplantation tolerance" *Curr. Opin. Immun.* 23 (2011) pp. 660-669.
Ritelli, et al. "Further delineation of Loeys-Dietz syndrome type 4 in a family with mild vascular involvement and a TGFB2 splicing mutation" *BMC Med. Genet.* 15:91 (2014) pp. 1-9.
Roncarolo, et al. "Clinical tolerance in allogeneic hematopoietic stem cell transplantation" *Immun. Rev.* 241 (2011) pp. 145-163.
Safinia, et al. "Successful expansion of functional and stable regulatory T cells for immunotherapy in liver transplantation" *Oncotarget* 7 (2016) pp. 1-15.
Safinia, et al. "Regulatory T cells: serious contenders in the promise for immunological tolerance in transplantation" Front. Immun. 6:438 (2015) pp. 1-16.
Sakaguchi, et al. "Regulatory T cells and immune tolerance" *Cell* 133 (2008) pp. 775-787.
Sebastian, et al. "Helios controls a limited subset of regulatory T cell functions" *J. Immun.* 196 (2016) pp. 144-155.
Seo, et al. "MicroRNA miR-466 inhibits Lymphangiogenesis by targeting prospero-related homeobox 1 in the alkali burn corneal injury model" *J. Biomed. Sci.* 22:3 (2015) pp. 1-12.
Shrestha, et al. "$T_{reg}$ cells require the phosphatase PTEN to restrain $T_H1$ and $T_{FH}$ cell responses" *Nat. Immun.* 16 (2015) pp. 178-187.
Sido, et al. "Δ9-Tetrahydrocannabinol attenuates allogeneic host-versus-graft response and delays skin graft rejection through activation of cannabinoid receptor 1 and induction of myeloid-derived suppressor cells" *J. Leukoc. Biol.* 98 (2015) pp. 435-447.
Smigielska-Czepiel, et al. "Comprehensive analysis of miRNA expression in T-cell subsets of rheumatoid arthritis patients reveals defined signatures of naive and memory Tregs" *Genes Immun.* 15 (2014) pp. 115-125.
Söderberg, et al. "Complex and context dependent regulation of hematopoiesis by TGF-β superfamily signaling" *Ann. N.Y. Acad. Sci.* 1176 (2009) pp. 55-69.
Tang, et al. "Transplant trials with Tregs: perils and promises" *J. Clin. Invest.* 127 (2017) pp. 2505-2512.
Tu, et al. "Regulatory T cells, especially ICOS+ FOXP3+ regulatory T cells, are increased in the hepatocellular carcinoma microenvironment and predict reduced survival" *Sci. Rep.* 6 (2016).
Van Der Net, et al. "Regulatory T cells: first steps of clinical application in solid organ transplantation" *Transpl. Int'l.* 29 (2016) pp. 3-11.
Vocanson, et al. "Inducible costimulator (ICOS) is a marker for highly suppressive antigen-specific T cells sharing features of $T_H17/T_H1$ and regulatory T cells" *J. Allerg. Clin. Immun.* 126 (2010) pp. 280-289.e7.
Wang, et al. "Mbd2 promotes Foxp3 demethylation and T-regulatory-cell function" *Mol. Cell Biol.* 33 (2013) pp. 4106-4115.
Xie, et al. "miR-599 inhibits vascular smooth muscle cells proliferation and migration by targeting TGFB2" *PLoS One* 10:e0141512 (2015) pp. 1-11.
Yadav, et al. "Neuropilin-1 distinguishes natural and inducible regulatory T cells among regulatory T cell subsets in vivo" *J. Exp. Med.* 209 (2012) pp. 1713-1722.
Zhang, et. "The expression of microRNA and microRNA clusters in the aging heart" *PLoS One* 7:e34688 (2012) pp. 1-13.
Zhang, et al. "Involvement of Foxp3-expressing $CD4^+$ $CD25^+$ regulatory T cells in the development of tolerance induced by transforming growth factor-β2-treated antigen-presenting cells" *Immunology* 124 (2008) pp. 304-314.
Zheng, et al. "Genome-wide impact of a recently expanded microRNA cluster in mouse" *PNAS* 108 (2011) pp. 15804-15809.

\* cited by examiner

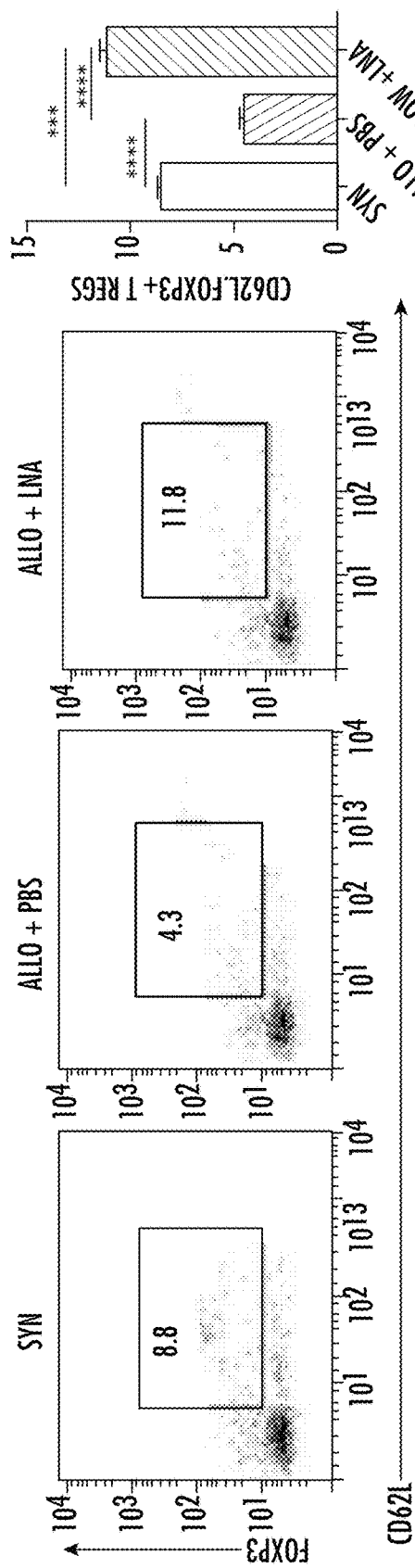
FIG. 6H
FIG. 6I
FIG. 6J

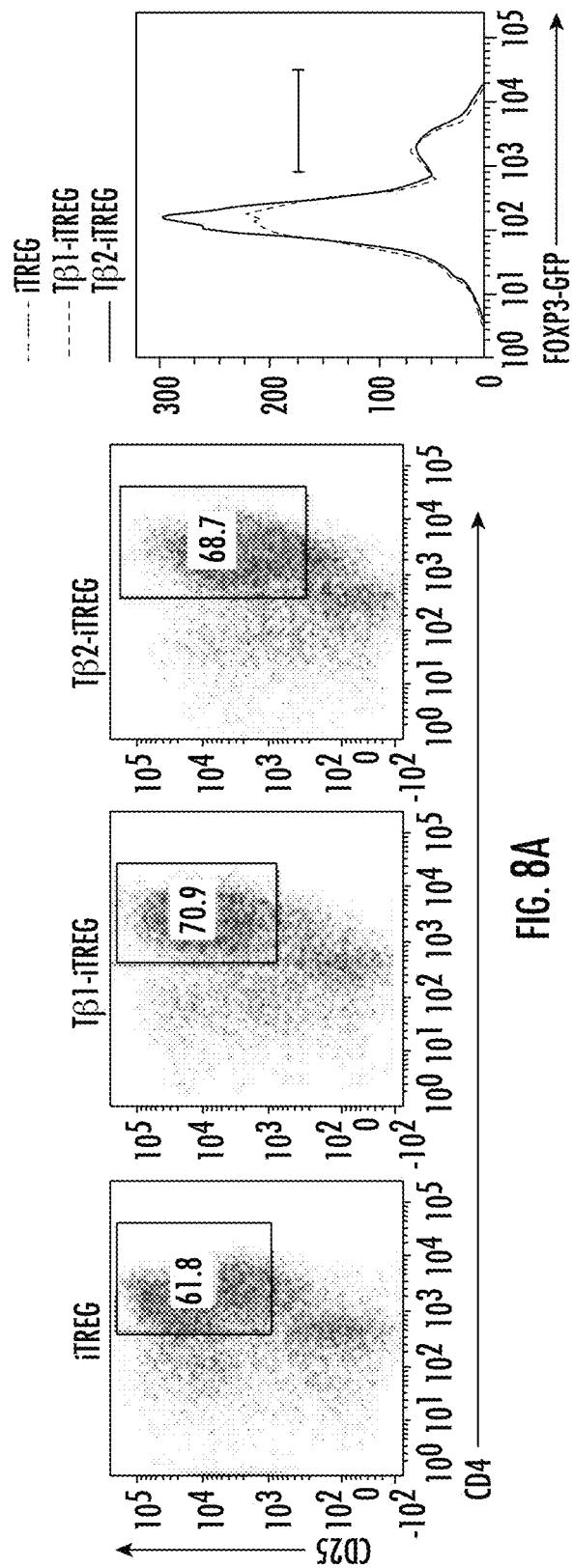

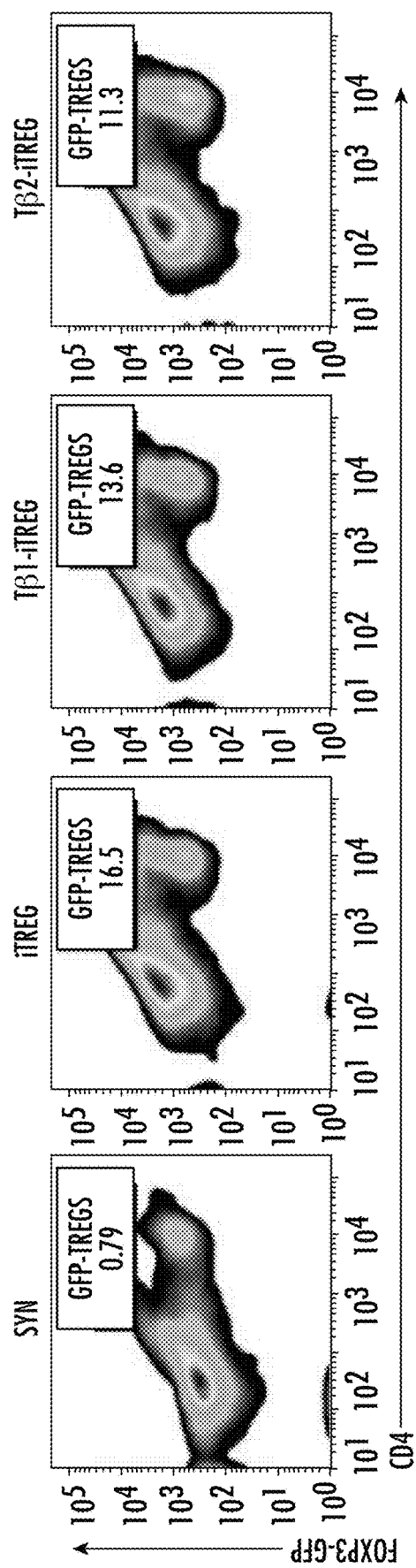
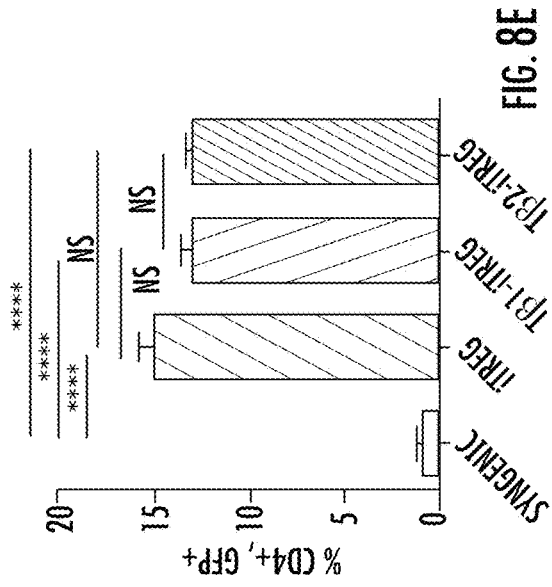
FIG. 8D
FIG. 8E

| PREDICTED miRNA TARGET | PREDICTED CONSEQUENTIAL PAIRING OF miRNA (TOP) AND mRNA TARGET REGION (BOTTOM) | mirSVR SCORE |
|---|---|---|
| TGFβ2 | 3' agAAUACACAGCAC-AUACAUAu 5' mmu-miR-466a-3p<br>860: 5' guUGACCUGU-UUUGAUAUGUAUu 3' TGFB2 | -0.5786 |
| TGFβRIII | 3' agaAUACACAGCACAUACAUAu 5' mmu-miR-466a-3p<br>1649: 5' ugaUAAGUAUAU-UCUAUGUAUa 3' TGFBR3 | -0.0256 |
| SMAD2 | 3' agaauacacacgcacaUACAUAu 5' mmu-miR-466a-3p<br>29: 5' cucgucguaguauucAUGUAUg 3' SMAD2 | -0.0256 |
| SMAD3 | 3' agaauacacacgcacaUACAUAu 5' mmu-miR-466a-3p<br>660:5' uggcaccacacccugAUGUAUa 3' SMAD3 | -0.3307 |

FIG. 9

COMPOSITIONS AND METHODS FOR INDUCING A TREG PHENOTYPE AND METHODS FOR USE FOR THE SAME

CROSS REFERENCE TO RELATED APPLICATION

This application claims filing benefit of U.S. Provisional Patent Application Ser. No. 62/808,403, having a filing date of Feb. 21, 2019, which is incorporated herein by reference for all purposes.

STATEMENT AS TO RIGHTS TO INVENTIONS MADE UNDER FEDERALLY SPONSORED RESEARCH

This invention was made with Government support under Contract No. 1P20GM103641, awarded by the National Institutes of Health (NIH) and Centers of Biomedical Research Excellence (COBRE). The Government has certain rights in the invention.

SEQUENCE LISTING

This application contains a Sequence Listing which has been submitted electronically in ASCII format and is incorporated herein by reference in its entirety for all purposes. Said ASCII copy, created on Nov. 20, 2019, is named USC-620_Sequence_List.txt and is 8,068 bytes in size.

BACKGROUND

T cell phenotype is important in controlling the immune response generated due to different stimuli. For example, viral infection requires the generation of cytotoxic or killer T cells that can destroy or induce the destruction of infected cells. While necessary to combat viral infections, the T cell response can pose problems when activated against non-pathogenic tissue such as in autoimmune diseases or transplant rejection.

Important in controlling the T cell response are regulatory T cells (Treg). These cells can act to suppress the immune response by secreting anti-inflammatory cytokines and/or decreasing the level of cytokine expression. Treg cells help to maintain tolerance to self-antigens, thereby allowing the immune system to recognize self from non-self.

The ability to adapt or change the immune response is especially important in cases such as organ transplantation. While graft loss due to acute rejection is rare due to the development of immunosuppressive drugs, there remains the issue of chronic rejection. Additionally, general immunosuppression can leave organ transplant patients vulnerable to infectious diseases.

MicroRNAs (miRNAs) are one of the critical players of T cell function and plasticity. miRNAs are a group of short, single-stranded ~21 nucleotide-long RNA sequences that bind to the 3' untranslated region (UTR) of target mRNAs through a 6-8 nucleotide 'seed sequence,' leading to degradation of target mRNA or inhibition of translation. Though important in T cell plasticity, there remains little information concerning miRNAs that may hinder or promote Treg generation in inflammatory models. Improving this understanding may provide novel treatments that can be used to supplement or provide an alternative to standard care in inflammatory diseases.

SUMMARY OF THE INVENTION

The present disclosure is directed to compositions and methods to induce a Treg phenotype in mammalian naïve CD4+ T cells. In certain embodiments, the methods and compositions described can be applied as methods to treat an inflammatory response that can present in certain diseases, autoimmune disorders, and/or transplant complications (e.g., lupus and graft-versus-host disease). Additionally, the embodiments of the disclosure may be used in combination with, but do not require, systemic immune suppression, such as a chemotherapeutic agent.

In one embodiment, a method can utilize transforming growth factor-beta 2 (referenced as TGF-$\beta$2 or TGFB2), molecules that stimulate the production of TGFB2, inhibitors of molecules that suppress production of TGFB2, or molecules that effect the function of TGFB2 to induce a Treg phenotype in naïve CD4+ T cells from a mammal. Provided herein are embodiments and examples demonstrating the production of Treg cells, as well as the application of Treg cells in modulating the inflammatory response present in certain diseases.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 6H illustrates flow cytometry dot plots of circulating cells double positive for FoxP3 and CD62L, data are gated on CD4+ cells.

FIG. 6I illustrates quantification of data of FIG. 6H.

FIG. 6J illustrates images of grafts excised from the mice. Data of FIGS. 6A-6J are presented as mean±SEM; n=at least 4 per group. *P<0.05, P<0.005, 851 *P<0.001, ****P<0.0001 by ANOVA with Tukey's multiple comparisons test.

FIG. 8A illustrates dot plots of CDF+CD25+ cells and providing support for demonstration that TGF-β2 induced Tregs are equally as potent as TGF-β1 induced Tregs in ameliorating allograft rejection. CD4+ cells were purified from naïve BL6 FoxP3GFP mice and cocultured with allogenic splenic APCs along with anti-CD3ε (10 μg/mL), anti-CD28 (4 μg/mL) and IL-2 (10 ng/mL). Tβ1, and Tβ2-iTregs were also administered TGF-β1 (5 ng/mL) or TGF-β2 (5 ng/mL), respectively. Coculture proceeded for 3 days at which point the cells were either stained for FoxP3GFP, or sorted into CD4+, FoxP3GFP+ cells and injected intravenously into graft-recipient mice 1 day before transplantation.

FIG. 8B illustrates a histogram for FoxP3GFP expression gated on dot plots of FIG. 8A.

FIG. 8C illustrates a survival plot of indicated groups of female C57BL/6 mice given either syn (BL6) or allo (C3H) tail skin grafts. Mice receiving allografts were administered $1 \times 10^6$ iTregs intravenously 1 day before transplant. Grafts were scored starting 7 days after transplantation and continued until mice were sacrificed on day 12. GICs, dLNs and blood were collected for flow cytometric analysis.

FIG. 8D illustrates density plots of GFP+, CD4+ co-expressing iTregs in the dLN.

FIG. 8E illustrates a bar graph displaying quantified flow cytometry results.

FIG. 9 illustrates a table displaying predicted miRNA target genes alongside predicted pairing region and a corresponding mirSVR score. FIG. 9 discloses SEQ ID NOs: 1, 33, 1, 34, 1, 35, 1, and 36, respectively, in order of appearance.

Figure 1A:
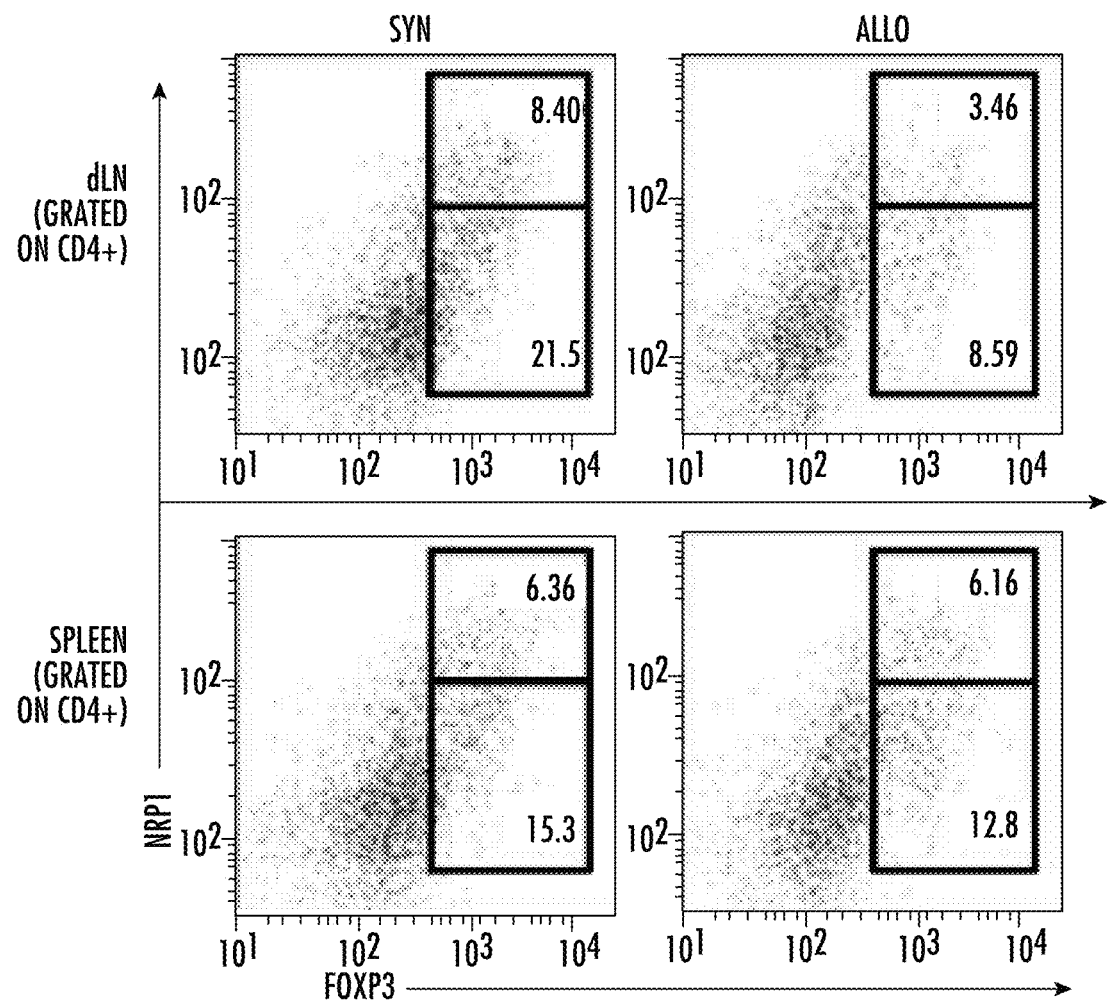
FIG. 1A illustrates representative flow cytometry dot plots gated on CD4+ cells, displaying the percentage of natural Tregs (nTreg) present through co-expression of CD4, FoxP3, and Nrp1 and the percentage of peripheral Tregs (pTreg) that are CD4 and FoxP3 positive and Nrp1LO or negative and provides support for the understanding that allografting alters the draining lymph node (dLN) regulatory T cell (Tregs) phenotype. Ten days after either syngeneic (syn) (BL6) or allogenic (allo) C3H (H-2k, C3H) skin transplants, mice were sacrificed, and organs of interest were harvested. Draining lymph nodes (dLNs) and spleens were analyzed for Treg cell phenotype by flow cytometry.
Figure 1B:
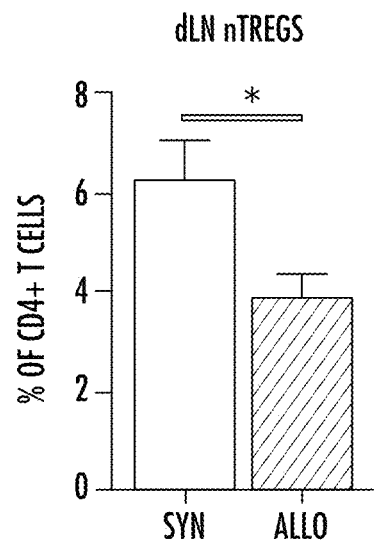
FIG. 1B illustrates a quantification of the flow cytometry results of FIG. 1A and provides a bar graph displaying example data comparing the frequency of nTregs in the dLNs.
Figure 1C:
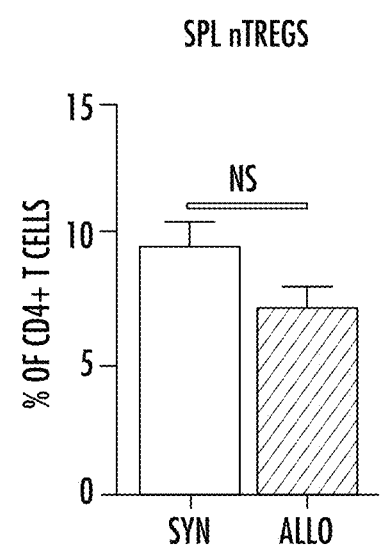
FIG. 1C illustrates a quantification of the flow cytometry results of FIG. 1A and provides a bar graph displaying example data comparing the frequency of nTregs in the spleen.
Figure 1D:
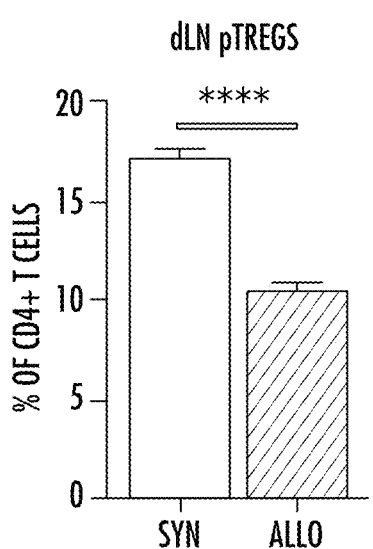
FIG. 1D illustrates a quantification of the flow cytometry results of FIG. 1A and provides a bar graph displaying example data comparing the frequency of pTregs in the dLN.
Figure 1E:
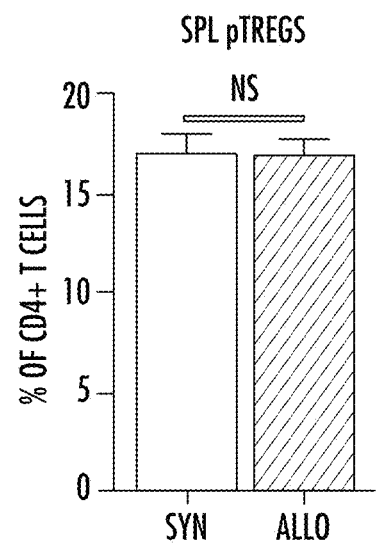
FIG. 1E illustrates a quantification of the flow cytometry results and provides a bar graph displaying example data comparing the frequency of pTregs in the spleen.

Repeat use of reference characters in the present specification and drawings is intended to represent the same or analogous features or elements of the present invention. In some instances, multiple notations can be used in the figures to represent the same compound or gene. For example, the cytokine and/or the gene encoding interferon gamma can be referenced using either IFNγ or IFNG both in the Drawings and in this disclosure including the claims. Other cytokines and their corresponding genes are represented using standard nomenclature. For example, the class of interleukins can be represented as IL followed by the representative number (e.g., interleukin 17 can be represented as IL-17.) Additionally, the class of cluster of differentiation surface markers can be represented as CD and a representative number (e.g., cluster of differentiation 28 can be represented as CD28.)

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only and is not intended as limiting the broader aspects of the present invention, which broader aspects are embodied exemplary constructions.

Generally speaking, the present invention is directed to compositions and methods for inducing a Treg phenotype in mammalian naïve CD4+ T cells. In certain embodiments, the methods and compositions described can be applied as methods to treat autoimmune disorders or transplant complications (e.g., lupus and graft-versus-host disease) and may be used in combination with, but do not require, systemic immune suppression, such as a chemotherapeutic agent. In particular, embodiments of the disclosure can utilize transforming growth factor-beta 2 (referenced as TGF-β2 or TGFB2), molecules that stimulate the production of TGFB2, inhibitors of molecules that suppress production of TGFB2, or molecules that effect the function of TGFB2 to induce a Treg phenotype in naïve CD4+ T cells from a mammal. Provided herein are embodiments and examples demonstrating the production of Treg cells, as well as the application of Treg cells in modulating the inflammatory response present in certain diseases.

In an example embodiment, a method for inducing a Treg phenotype in naïve CD4+ T cells includes delivering TGFβ2, a miRNA inhibitor, a miRNA, a miRNA mimic, a compound targeting a portion of TGFBR3, or any combination of these to the naïve CD4+ T cells.

In certain embodiments, the method for inducing a Treg phenotype in naïve CD4+ T cells can further include extracting naïve CD4+ T cells from a mammal (e.g., a human, rodent, monkey, canine, feline, ovine) and culturing the naïve CD4+ T cells in the presence of one or more compounds from the group: a compound targeting a portion of the CD3 receptor, a compound targeting a portion of the CD28 receptor, and IL-2. For some of these embodiments, the method can be referred to as in vitro induction as the method for inducing a Treg phenotype occurrence in culture instead of in the mammal.

As an example implementation, the compound targeting a portion of the CD3 receptor can be a compound generating an activating signal or producing a conformational change such that binding to an epitope present on the CD3 receptor produces an activation signal (e.g., through promoting the binding of an adaptor protein such as Nck.) For instance, the compound targeting a portion of the CD3 receptor can include one or more antibody from the group consisting of: anti-CD3e, anti-CD3g, and anti-CD3d.

In another example implementation, the compound targeting a portion of the CD28 receptor can include be a compound generating an activating signal or producing a conformational change such that binding to an epitope present on the CD28 receptor produces an activation signal (e.g., by mimicking the binding of a B7 membrane protein). For instance, the compound targeting a portion of the CD28 receptor can include an antibody such as anti-CD28.

For embodiments of the disclosure, overlap in the activation and differentiation pathways that comprise the inflammatory response generated by the immune system allows the practice of the disclosed embodiments in various mammals that include, but are not limited to, humans, apes, monkeys, mice, rates, dogs, and cats.

In embodiments of the disclosure, TGFB2 can be present at a concentration in the range of about 0.5 ng/mL to about 40 ng/mL. For example, a culture containing naïve CD4+ T-cells extracted from a mammal can include a growth media containing buffers, salts, and glucose. During induction, TGFB2 can be added to the growth media at a concentration of about 0.5 ng/mL to about 40 ng/mL based on the volume of growth media. In some embodiments, the concentration of TGFB2 can be about 1 ng/mL to about 30 ng/mL. In certain embodiments, the concentration of TGFB2 can be about 5 ng/mL to about 20 ng/mL.

In an embodiment of the disclosure, the mammal is a mouse and the miRNA inhibitor includes a complementary sequence to one or more miRNA from the group: miR-324-3p, miR-18a-5p, miR-484, miR-466a-3p, miR-466e-3p, miR-27b-3p, miR-194-5p, miR-181c-5p, miR-467a-5p, miR-128-3p, miR-27a-3p, miR-421-3p, miR-19b-3p, miR-466b-3p, miR-466c-3p, miR-466c-3p, miR-466p-3p, miR-192-5p, miR-182-5p, let-7f-5p, miR-30b-5p, miR-30e-5p, miR-21a-5p, miR-30a-5p, miR-467c-5p, miR-669a-3p, miR-6690-3p, miR-467a-1, miR-15a-5p. In certain instances, the miRNA inhibitor can include a locked nucleic acid (LNA) oligonucleotide that contains one or more nucleotide building blocks having an extra methylene bridge.

In some instances, the miRNA inhibitor can include a substantially complementary sequence. As an example, miR-466a-3p includes the sequence UAUACAUA-CACGCACACAUAAGA (SEQ ID NO: 1) (miRNA sequences can be found using a database such as miRbase.org or TargetScan) which has the following complementary sequence based on nucleobase paring rules: ATATGTATGTGCGTGTGTATTCT (SEQ ID NO: 2). For embodiments of the disclosure, the substantially complementary sequence can include the complementary sequence or a modified complementary sequence. The modified complementary sequence can include one or more additions, deletions, or substitutions to modify the complementary sequence without reducing the ability to bind and inhibit the miRNA sequence. Using the same example complementary sequence, a substantially complementary sequence can include an addition (e.g., ATATGTATGTGCGTGTGTAT-TCT<u>C</u> (SEQ ID NO: 3)), a deletion (e.g., ATAT<s>G</s>TATGTGCGTGTGTATTCT (SEQ ID NO: 4)), a substitution (e.g., ATATGTATGTGCGTGTGTAT∓<u>U</u>CT (SEQ ID NO: 5)), or combinations of these modifications to produce the modified complementary sequence.

In some embodiments, the number of modifications that still result in inhibition can be determined using an analytical technique, including, but not limited to, a circular dichroism (CD) spectrometry or calorimetry. These example techniques can also be used to determine the binding strength of an inhibitor designed to target a miRNA sequence, and thus, can be applied with other oligonucleotide structures such as LNA.

In another embodiment of the disclosure, the mammal is a human and the miRNA inhibitor comprises a complementary or a substantially complementary sequence to one or more miRNA from the group: miR-194-5p, miR-19b-3p, miR-21-5p, miR-182-5p, miR-15a-5p. As an example, miR-19b-3p includes the sequence UGUGCAAAUC-CAUGCAAAACUGA (SEQ ID NO: 6) (miRbase), which has the following complementary sequence: ACACGTT-TAGGTACGTTTTGACT (SEQ ID NO: 7). As described above, embodiments of the disclosure may utilize a substantially complementary sequence as the miRNA inhibitor. For these embodiments, the substantially complementary sequence can include one or more modifications such as an addition, a deletion, and/or a substitution.

In an embodiment of the disclosure, the mammal is a mouse and the miRNA or the miRNA mimic comprises a sequence substantially corresponding to one or more miRNA from the group: miR-1291, miR-5112, miR-6368, miR-7011-5p, miR-1894-3p, miR-6912-5p, miR-6937-5p, miR-6971-5p, miR-7016-5p, miR-7648-3p. As an example, miR-6368 includes the sequence CUGGGAAGCAGUG-GAGGGGAG (SEQ ID NO: 8). Using the same example sequence, a substantially corresponding sequence can include the original sequence (i.e., CUGGGAAGCAG UGGAGGGGAG (SEQ ID NO: 8)), or the original sequence having an addition (e.g., CUGGGAAGCAGU GGAGGGGAG<u>C</u> (SEQ ID NO: 9)), a deletion (e.g., CUGGGAAGCAGUGGAGG<s>G</s>AG (SEQ ID NO: 10)), a substitution (e.g., CU<s>G</s><u>C</u>GGAAGCAGUGGAGGGGAG (SEQ ID NO: 11)), or combinations of these variations.

In another embodiment of the disclosure, the mammal is a human and the miRNA or the miRNA mimic comprises a sequence substantially corresponding to miR-1291. As an example, miR-1291 includes the sequence UGGCC-CUGACUGAAGACCAGCAGU (SEQ ID NO: 12), and for these embodiments, the substantially corresponding sequence can include the original sequence or in some embodiments, the original sequence having one or more modifications such as an addition, a deletion, and/or a substitution.

Generally, the miRNA mimic can include a structure or structures similar to any of the miRNA disclosed herein. Development and/or structures for the miRNA mimics can include an artificially synthesized RNA sequence that differs in at least one base pair so that the mimic is only partially similar to the miRNA oligonucleotide sequence. Alternative structures for the miRNA mimics can include substituting uracil bases in the miRNA structure for thiamine bases in the mimic structure. Additional modifications to the miRNA structure that can produce a miRNA mimic may include alkylating (e.g., methylation) one or more hydroxyl groups and/or one or more amine groups of the miRNA structure.

Additionally, or alternatively, certain embodiments of the disclosure can include a compound targeting a portion of the transformation growth factor beta 3 receptor (TGFBR3.) As an example embodiment, the compound can include an antibody specific to an epitope on the TFGBR3 protein.

Certain embodiments of the disclosure can also provide methods for treating an inflammatory response by treating a mammal or cells extracted from the mammal using any of the prior methods.

As an example embodiment, a method for treating an inflammatory response in a mammal (e.g., a human, mouse, dog, cat, cow, or sheep) can include administering a composition to the mammal, the composition containing TGFB2, a miRNA inhibitor, a miRNA, a miRNA mimic, or combinations thereof. For instance, the micro-RNA inhibitor can include a locked nucleic acid or a substantially complementary sequence targeting a micro-RNA (e.g., miR-21-5p, miR-466a-3p, and miR-466e-3p, or another miRNA disclosed herein).

Alternatively, or additionally, administering the composition can include delivering a vector, including heterologous DNA expressing one or more of the group: TGFB2, a miRNA inhibitor, a miRNA, a miRNA mimic, or combinations thereof. For instance, the micro-RNA inhibitor can include a complementary sequence or a substantially complementary sequence targeting a micro-RNA (e.g., miR-194-5p, miR-19b-3p, miR-21-5p, miR-182-5p, miR-15a-5p, or other miRNA disclosed herein).

As an example implementation of delivering a vector, miR-21-5p may be utilized in conjunction with a suitable expression system, and a quantity of miR-21-5p nucleic acids can be generated from such expression systems. Recombinant expression is usefully accomplished using a vector, such as a plasmid. The vector can include a promoter operably linked to a sequence encoding a miR-21-5p nucleic acid. The vector can also include other elements required for transcription and translation. As used herein, vector refers to any carrier containing exogenous DNA. Thus, vectors can generally refer to agents that transport the exogenous nucleic acid into a cell and can include a promoter yielding expression of the nucleic acid in the cells into which it is delivered. Vectors include, but are not limited to, plasmids, viral nucleic acids, viruses, phage nucleic acids, phages, cosmids, and artificial chromosomes. A variety of prokaryotic and eukaryotic expression vectors suitable for carrying, encoding and/or expressing miR-21-5p nucleic acids are encompassed herein. Such expression vectors include, for example, pET, pET3d, pCR2.1, pBAD, pUC, and yeast vectors.

A variety of regulatory elements can be included in an expression cassette and/or expression vector, including promoters, enhancers, translational initiation sequences, transcription termination sequences, and other elements.

The expression of miR-21-5p from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter, and a synthetic promoter regulated by CRE. Vectors for bacterial expression include pGEX-5X-3, and for eukaryotic expression include pCIneo-CMV.

Generally, methods for treating an inflammatory response can be used with mammals that have been diagnosed with or that exhibit symptoms of a disease state. Some example disease states can include graft-versus-host disease and autoimmune conditions (e.g., arthritis, psoriasis, lupus, celiac disease, diabetes mellitus type 1, Grave's disease, inflammatory bowel disease, and multiple sclerosis).

Another example embodiment of the disclosure includes a method for treating a patient having allograph rejection at a graft site. The method for treating can include isolating CD4+ naïve T cells from the patient, inducing a Treg phenotype in the CD4+ naïve T cells by providing TGFB2 to the CD4+ naïve T cells, and reintroducing the induced Treg cells to the patient at an administration site.

For these embodiments, the administration site can include the spleen, a draining lymph node, and the graft site, or combinations of these sites. In some embodiments, the draining lymph node to which the Treg cells are administered is the draining lymph node nearest to the graft site. In some embodiments, the Treg cells can be administered to multiple draining lymph nodes.

In combination with the reintroduction of the induced Treg cells, in some embodiments the patient can further receive a secondary treatment. Example secondary treatments can include administering to the patient miRNA, a miRNA mimic, and/or a miRNA inhibitor as described in the examples and embodiments set forth herein. In an example implementation, the method for treating a patient can include co-administering (i.e., at substantially the same time) the induced Treg cells with a miRNA inhibitor having a substantially complementary sequence to one or more miRNA disclosed herein (e.g., miR-21-5p).

Embodiments of the disclosure that provide methods for treating an inflammatory response or treating a patient having allograft rejection can be used in combination with current standards of care including, but not limited to, immunosuppressive drugs, chemotherapeutics, non-steroidal anti-inflammatory compounds (NSAIDs), and/or antibodies.

Example 1

Example 1 discusses various methods and procedures and provides exemplary embodiments that may be understood in conjunction with the Drawings and Description provided herein. The specific methods and procedures described in Example 1 are not meant to limit the disclosure and are provided solely to illustrate some of the ways in which the invention may be practiced.

Methods

Animals

The University of South Carolina Institutional Animal Care and Use Committee approved all experiments. All mice were housed at the AAALAC-accredited animal facility at the University of South Carolina, School of Medicine (Columbia, S.C.) and given ad libitum access to water and normal chow diet. Female C57BL/6 (H-2b wild-type, BL6) and C3H (H-2k, C3H) mice, aged 8-12 weeks, with an average weight of 20 g, were obtained from Jackson Laboratories (Bar Harbor, Me., USA). C57BL/6-FoxP3GFP mice were bred and maintained in-house. The number of mice for each experimental cohort is described in the figure legends. Each experiment was repeated at least twice, and in many cases, three or four times.

Skin Transplant, LNA-Based Treatment, and Adoptive iTreg Transfer

Transplantation of tail skin from donor (C3H, allograft; C57BL/6, syngeneic graft) to recipient C57BL/6 mice was carried out as described previously (61). Skin grafts were obtained by excising the tail from donor mice and splitting the tail into equivalently sized grafts. Recipient mice were anesthetized by an intraperitoneal injection of ketamine (80 mg/kg) and xylazine (12 mg/kg) (Southern Anesthesia & Surgical, Columbia, S.C.) in molecular-grade water. Upon sufficient anesthetic depth, mice were shaved and ~1×1 cm$^2$ graft beds were made using curved scissors on the dorsal lateral surface. Donor skin grafts were placed onto the graft beds and mice were bandaged. Mice were monitored and kept in bandages for 7-9 days following skin transplantation surgery. In studies using Locked Nucleic Acid (LNA)-based miRNA inhibitor (anti-miR-466a-3p, Exiqon), the LNA (10 mg/kg) was injected i.p. to graft recipient mice 1 day before skin transplant and then every 3rd day after that until termination of the study. For studies involving expanded iTregs, these cells were cultured as described below, sorted for CD4+, FoxP3-GFP expression using BD FACSAria II, and 1×10$^6$ iTregs were adoptively transferred 1 day before skin-grafting. For graft rejection scoring, mice were scored as +/+, viable graft; +/−, partially rejected the graft (≥50% scabbed over or necrotic, or ≥50% reduction in graft size); or −/−, fully rejected the graft (≥80% necrotic). For depicting graft survival, +/+ and +/− skin grafts were considered viable, and −/− skin grafts were considered nonviable. The log-rank method was used to determine differences in graft survival.

Target Prediction and Luciferase Reporter Assays

Relevant targets for miR-466a-3p and other miRNAs were investigated using predictions from TargetScan Mouse 6.2 software and microRNA.org. The 3' UTR of candidate gene targets or mutated control were purchased from Integrated DNA Technologies (IDT) and cloned immediately downstream of luciferase in the pMiReport vector (Promega, Madison, Wis., USA). Insertion of candidate mRNAs was verified through PCR and agarose gel electrophoresis. For luciferase assays, 2.5×10$^5$ EL-4 cells were plated in 24-well plates for 24 hours and subsequently transfected with either luciferase reporter constructs, together with miR-466a-3p mimics or the negative scramble control (Qiagen, Valencia, Calif.) using lipofectamine 3000 (Life Technologies). At 48 hours post-transfection, dual luciferase assay system (Promega, Madison, Wis., USA) was used to detect luciferase activity. Normalized data were calculated as the quotient of Renilla/firefly luciferase activities. The experiments were performed in duplicate and repeated at least 3 times.

Cell Culture

Cells were cultured in a sterile incubator that was maintained at 37° C. and 5% CO$_2$. EL-4 cells were cultured in DMEM supplemented with 10% fetal bovine serum, 100 U/mL penicillin, and 100 U/mL streptomycin. Primary cells were cultured in complete RPMI supplemented with 10% FBS, 100 U/mL penicillin, 100 U/mL streptomycin (both Gibco), 10 mM HEPES (Gibco, Paisley, UK), 50 µM β-mercaptoethanol (Sigma-Aldrich, Gillingham, UK), and appropriate growth cytokines as needed for the experiment (complete medium).

Treg Polarization, CD3/CD28 Stimulation and miRNA Transfection

For Treg polarization and CD3/CD28 stimulation studies, naïve lymph nodes were harvested and processed into single-cell suspensions. CD4+ T cells were purified using EasySep™ PE Positive Selection Kit (Stemcell Technologies, 18557). CD4+ T cell purity was routinely >90% as verified through flow cytometry. Cells (1×106) were plated in 12-well plates in complete medium supplemented with plate-bound anti-mouse CD3ε, clone 145-2C11 (3 µg/mL) in the presence of anti-mouse CD28, clone 37.51 (3 µg/mL). For studies examining only CD23/CD28 stimulation, cells were harvested 48 hours after plating for downstream analysis. For Treg polarization, cells were plated with recombinant mouse IL-2 (5 ng/mL) and recombinant human TGF-β1 (5 ng/mL), or recombinant TGF-β2 (5 ng/mL) (R&D Systems, Minneapolis, Minn.) where indicated, in addition to the aforementioned amounts of CD3 and CD28. Five days after plating, cells were harvested for downstream analysis and cell culture supernatants were collected for ELISAs. Antibodies (e.g., anti-mouse CD3 and anti-mouse CD28) and cytokines were purchased from Biolegend (San Diego, Calif.). In both experiments, cells were transfected with either 25 nM miR-466a-3p mimic (UAUACAUA-CACGCACACAUAAGA (SEQ ID NO: 1)), 100 nM miR-466a-3p inhibitor (ATATGTATGTGCGTGTGTATTCT (SEQ ID NO: 2)), or 25 nM scramble control, using HiPerFect Transfection Reagent from Qiagen (Valencia, Calif.). Transfection efficiency was validated using qRT-PCR.

iTreg Generation

CD4+ T cells from BL6 FoxP3GFP mice were purified using EasySep™ PE Positive Selection Kit (Stemcell Technologies, 18557). Cd11c+ allogenic APCs were isolated from the spleens of C3H mice using EasySep™ PE Positive Selection Kit. The cells were co-cultured for 3 days at a ratio of 5:1, T cells: APCs. Additionally, anti-CD3ε (10 µg/mL), anti-CD28 (4 µg/mL) and IL-2 (5 ng/mL) were added to all wells, and TGF-β1 (5 ng/mL) and TGF-β2 (5 ng/mL) were added where indicated. Cells were co-cultured for 72 hours before being collected for downstream analysis or sorted for purity and injected intravenously.

Alloantigen Co-Culture

Naïve lymph node cells were harvested and processed through a 100 µm cell strainer to make single-cell suspensions. Cells (1×10$^6$) were plated in the presence of 50 µg/mL of alloantigen or no antigen (control) in complete RPMI in 12-well plates for 10 days. Fresh medium was added on day 5, and LNA-based miRNA inhibitor (anti-miR-466a-3p, Exiqon, Denmark) and control LNA were added every 3 days at 50 ng/mL. After 10 days, cells were collected for downstream analysis and cell culture supernatants were stored at −20° C. before being analyzed by cytokine-specific ELISA.

Alloantigen Preparation (Splenocyte Lysates)

C3H mice were euthanized and their spleens were aseptically removed, homogenized, and passed through a 100 µm cell strainer to make single-cell suspensions in cold, serum-free media. Red blood cells (RBCs) were lysed and the cell suspension was washed twice with cold serum-free media. Then, cells were re-suspended at a cellular density of 1×108 cells/mL and subjected to four freeze (5 minutes liquid nitrogen)—thaw (10 minutes 37° C. water bath) cycles. Cells were then sonicated for 5 minutes, and the lysate was centrifuged at 300 rpm (10 minutes, 4° C.) and supernatant was recovered. The lysate was filtered with a 0.22 μm microporous membrane, protein concentration was checked using Qubit fluorometer (Thermo Fisher Scientific), and subsequently stored at 4° C.

Graft Infiltrating Cell Extraction

Mice that received a skin-transplant were sacrificed and the transplanted graft was aseptically excised. Grafts were cut longitudinally, minced, and digested for 2 hours at 37° C. 5% $CO_2$ in PBS containing Type I Collagenase (2.5 mg/mL) and Hyaluronidase (0.25 mg/ml) (both from Sigma). Subsequently, graft infiltrating cells (GICs) were obtained by spinning at 1000 g for 7 minutes at 4° C. before being re-suspended in FACS buffer and live cells enumerated using a hematocytometer, and either stained immediately for flow cytometry or plated overnight to recover GIC culture supernatants. Cell-free culture supernatants were recovered and stored at −20° C. before being analyzed by cytokine-specific ELISA.

Flow Cytometry and Antibodies

Relevant tissues were harvested, and cells were homogenized and subsequently depleted of red blood cells as described above. Antibodies used for flow cytometric analysis (BioLegend, San Diego, Calif., USA) include Fc block, PE, PE/Cy7 and APC-Cy7-conjugated anti-CD4 (GK1.5), PE and BV 421-conjugated CD304 (Neuropilin-1) (3E12), PE-conjugated anti-IL-17A (TC11-18H10.1) Alexa Fluor® 488 and BV421-conjugated FoxP3 (MF-14), FITC conjugated Helios (22F6), APC conjugated IFNγ (XMG1.2), APC and PerCP-Cy5.5-conjugated LAP (TGF-β1) (TW7-16B4), FITC conjugated CD8a (53-6.7), BV 650-conjugated CD223 (LAG-3) (C9B7W), Alexa Fluor® 700-conjugated CD49b. PE conjugated IL-10 (JESS-16E3), PE conjugated GATA3 (16E10A23), FITC conjugated T-bet (4B10), APC conjugated CD62L (MEL-14), BV650 conjugated CD278 (ICOS)(DX29), (PE conjugated CD44 (IM7) and PE/Cy7 and BV 786-conjugated CD25 (3C7). Antibodies against nuclear proteins were probed using True-Nuclear™ Transcription Factor Buffer Set (BioLegend, San Diego, Calif., USA) and intracellular cytokine staining was performed using Fixation/Permeabilization Solution Kit (BD, San Jose, Calif.). The stained cells were then assessed by flow cytometer (FC500; Beckman Coulter, Brea, Calif., USA) or BD FACSCelesta (BD, San Jose, Calif., USA), and the resulting data analyzed by Cytomics CXP software (Beckman Coulter), DIVA software, or FlowJo. Sorting of cells was performed using a BD FACSAria™ II (BD, San Jose, Calif., USA).

miRNA Expression Profiling dLN CD4+ T cells purified to >90% purity using Easy-Sep™ PE Positive Selection Kit (Stemcell Technologies, 18557) were subject to total RNA isolation using miRNeasy kit (Qiagen, Valencia, Calif.), following manufacturer's protocol. The concentration and purity of the isolated RNA were determined using a spectrophotometer, and the integrity of the RNA was verified by Agilent 2100 BioAnalyzer (Agilent Tech, Palo Alto, Calif.). Profiling of miRNA expression from samples was performed using the Affymetrix GeneChip® miRNA 4.0 array platform (Affymetrix, Santa Clara, Calif.). This array version covers all mature miRNA sequences in miRBase Release 20. Total RNA was labeled with FlashTag™ Biotin HSR labeling kit from Affymetrix (Santa Clara, Calif.) according to manufacturer's instructions. Briefly, RNA spike control oligos were added to the RNA and incubated with a Poly A Tailing master mix for 15 min. Next, the RNA was labeled with biotin using FlashTag™ Biotin HSR Ligation mix. For hybridization of the biotin-labeled samples to the array, a GeneChip® Eukaryotic Hybridization Control kit comprising of bioB, bioC, bioD, and cre was used to create the array hybridization cocktail. Following incubation at 99° C. for 5 minutes, then 45° C. for 5 minutes, a small volume (100 μl) was injected into an array. The arrays were further incubated at 48° C. and 60 rpm for 16-18 hours. Post-hybridization, the array was washed and stained with fluorescent-conjugated streptavidin using the GeneChip® Fluidics Station 450. The stained chip was scanned on a GeneChip® Scanner (Affymetrix) to generate the data summarization, normalization, and quality control files. miRNA fold changes were obtained from the array and miRNAs with only a greater than 1.5-fold change were considered for further analysis. Predicted miRNA targets, alignments, and mirSVR scores were determined using an online miRNA database (microrna.org). Heatmap was made using Genesis software (Graz University of Technology).

Immunoblotting

Cell extracts were collected using RIPA lysis buffer (Sigma). Protein concentration was measured using Qubit fluorometer (Thermo Fisher Scientific) and were subjected to gel-electrophoresis and transfer onto a nitrocellulose membrane. Blots were blocked with 5% BSA in TBST, washed, and probed overnight at 4° C. with antibodies against TGFβ2 (1:1000, R&D Systems, MAB73461), TGFβR3 (1:2000, R&D Systems, AF5034), Smad2/3 (1:1000, CST, 5678), Phospho-Smad2 (Ser465/467)/Phospho-Smad3 (Ser423/425), (1:1000, CST, 8828), Smad4 (1:1000, CST, 38454) and Phospho-Smad4 (Thr276), (1:1000, Thermo Fisher Scientific, PAS-64712). The next day, blots were washed in TBST and then incubated at room temperature for 1 hour with a horseradish peroxidase labeled secondary antibody. Following secondary antibody incubations, blots were washed multiple times with TBST, exposed to a chemiluminescent reaction, and were exposed to film. Optical densities of films were quantified (sample minus background) using ImageJ.

Measurement of Cytokines

Cell culture supernatants from indicated in vitro experiments, graft infiltrating cell culture supernatants obtained ex vivo, or serum samples were analyzed for the following cytokines: IFNγ, TNFα, total TGF-β1, latent TGF-β1, and free-active TGF-β1, enzyme-linked immunosorbent assay (ELISA) kits were purchased from Biolegend (San Diego, Calif.). For detection of TGF-β2, ELISA kit was purchased from R&D Systems (Minneapolis, Minn.).

RNA Extraction and qPCR

Cell CD4+ T cells in the dLN or spleens of grafted mice were purified using EasySep™ PE Positive Selection Kit (Stemcell Technologies, 18557), and total RNA was isolated using miRNeasy kit (Qiagen, Valencia, Calif.), following manufacturer's protocol. Expression of indicated mRNA and miRNA levels were determined by quantitative real-time PCR (qRT-PCR). Quality and amount of RNA was investigated using NanoDrop™ 2000 (Thermo Fisher Scientific, Rockford, Ill.). For miRNA expression analysis, cDNA was made from total RNA using miRNA cDNA Synthesis Kit, with Poly(A) Polymerase Tailing (ABM, Canada, G902). qRT-PCR was carried out using EvaGreen® miRNA MasterMix (ABM, Canada, MasterMix-mS) with mouse primers for SNORD96A (control), miR-466a-3p, miR-466e-3p, miR-466p-3p, miR-15a-5p, miR-181c-5p, miR-27a-3p and miR-19b-3p (ABM, Canada). Expression levels were normalized to SNORD96A. For mRNA expression analysis, cDNA was made from total RNA using miScript cDNA synthesis kit from Bio-Rad (Hercules, Calif.). qRT-PCR was carried out using SsoAdvanced™ Universal SYBR® Green Supermix from Bio-Rad (Hercules, Calif.) with mouse primers for TGFβ1, TGFβ2, TGFβR3, PTEN, FoxP3, Smad2, Smad3, TGFβR1 and TGFβ3. Expression levels were normalized to β-actin mRNA levels. Fold changes were calculated using the 2−ΔΔCT method. Primers are detailed in Table 1.

TABLE 1

| Gene | Primer | Sequence (5'-3') |
|---|---|---|
| B actin | Forward | GGCTGTATTCCCCTCCG (SEQ ID NO: 13) |
|  | Reverse | CCAGTTGGTAACAATGCCATGT (SEQ ID NO: 14) |
| PTEN | Forward | TGGATTCGACTTAGACTTGACCT (SEQ ID NO: 15) |
|  | Reverse | GCGGTGTCATAATGTCTCTCAG (SEQ ID NO: 16) |
| FoxP3 | Forward | CAGCTGCAGCTGCCCACACTG (SEQ ID NO: 17) |
| FoxP3 cont. | Reverse | GCCTTGAGGGAGAAGACC (SEQ ID NO: 18) |
| TGF-β3 | Forward | AACAGCCACTCACGCACAGTG (SEQ ID NO: 19) |
|  | Reverse | GCACAACGAACTGGCTGTCTG (SEQ ID NO: 20) |
| TGF-β2 | Forward | AAGACTATCGACATGGAGCTG (SEQ ID NO: 21) |
|  | Reverse | GTACCGCTTCTCGGAGCTCTG (SEQ ID NO: 22) |
| TGF-βR1 | Forward | TCTGCATTGCACTTATGCTGA (SEQ ID NO: 23) |
|  | Reverse | AAAGGGCGATCTAGTGATGGA (SEQ ID NO: 24) |
| TGF-βR3 | Forward | GGTGTGAACTGTCACCGATCA (SEQ ID NO: 25) |
|  | Reverse | GTTTAGGATGTGAACCTCCCTTG (SEQ ID NO: 26) |
| TGF-β1 | Forward | GAGAAGAACTGCTGTGTGCG (SEQ ID NO: 27) |
|  | Reverse | GTGTCCAGGCTCCAAATATAGG (SEQ ID NO: 28) |
| Smad2 | Forward | ATTCCAGAAACGCCACCTCC (SEQ ID NO: 29) |
|  | Reverse | GCTATTGAACACCAAAATGCAGG (SEQ ID NO: 30) |
| Smad3 | Forward | GCGTGCGGCTCTACTACATC (SEQ ID NO: 31) |
|  | Reverse | GCACATTCGGGTCAACTGGTA (SEQ ID NO: 32) |

H&E Staining

Grafts were excised and fixed by immersion in 4% paraformaldehyde (PFA) in PBS, overnight. Fixed tissues were embedded in paraffin, sectioned, and stained with hematoxylin and eosin. Color bright field images and picture montages were taken using a Cytation™ 5 Imaging Reader (BioTek Instruments, Winooski, Vt., USA).

Results

Results provided in the drawings and described herein are meant to be exemplary and are not intended to limit the methods and compositions to modifications or alternatives as would be understood by a person of ordinary skill in the field of endeavor.

Draining Lymph Node T Regulatory Cell Response to Allograft

Figure 1F:
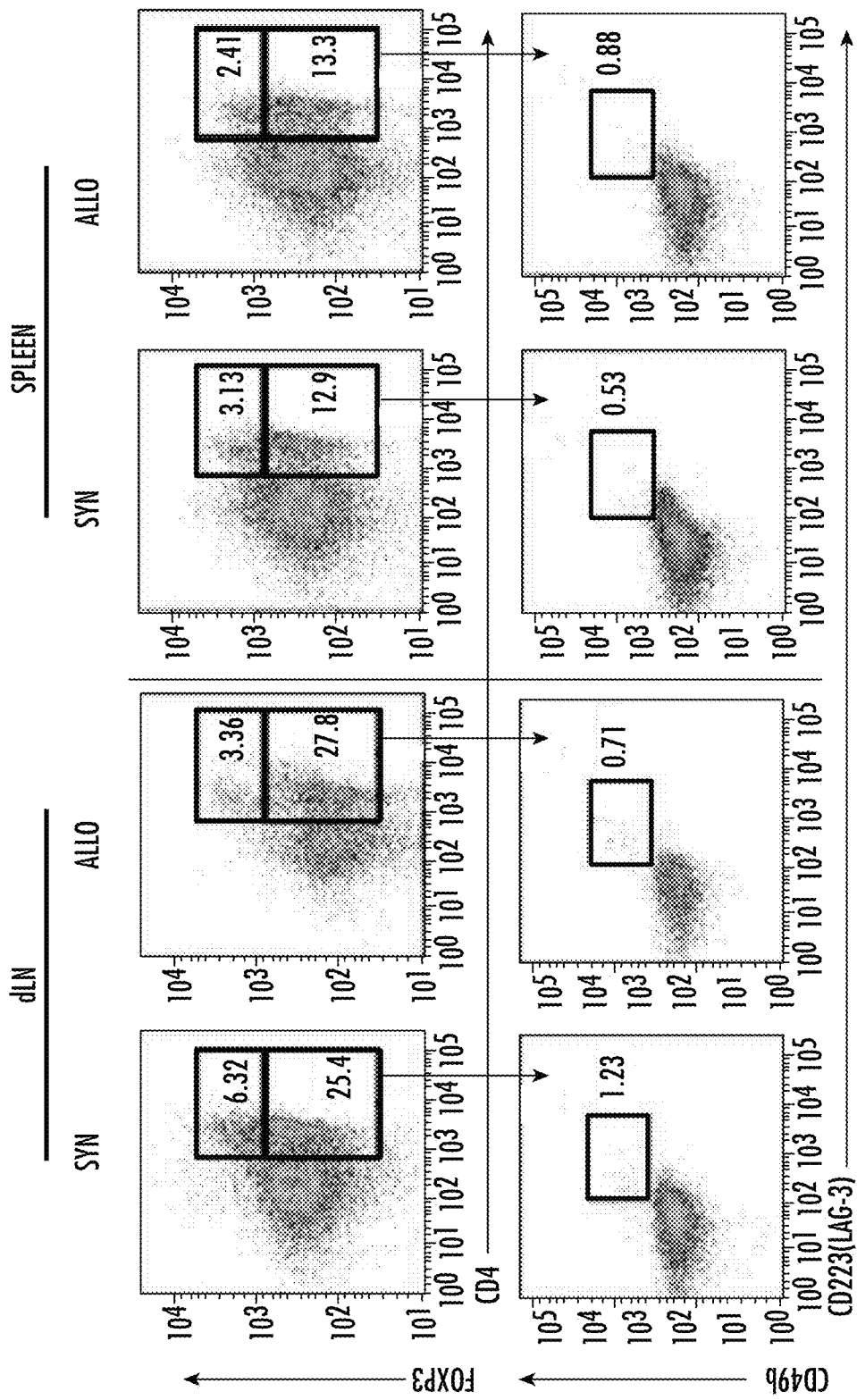
FIG. 1F illustrates dot plots (lower panels) gated on CD4+, FoxP3− cells (upper panel), displaying CD223 (LAG-3), CD49b double-positive Tr1 cells.
Figure 1G:
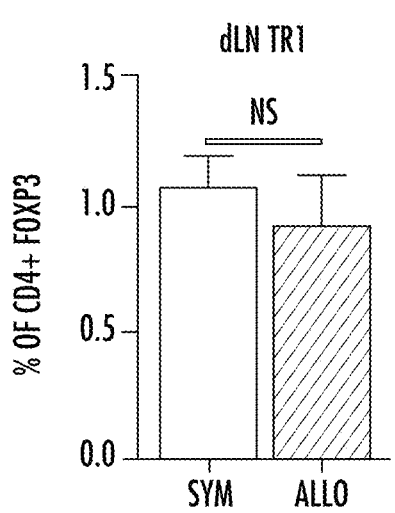
FIG. 1G illustrates a quantification of the flow cytometry results and provides a bar graph displaying example data comparing the frequency of TR1 cells in the dLN as determined by % of CD4+ FoxP3−.
Figure 1H:
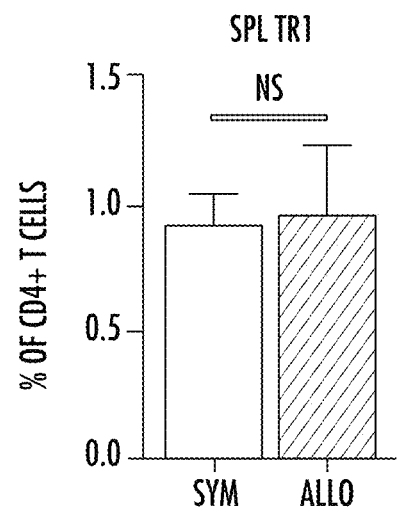
FIG. 1H illustrates a quantification of the flow cytometry results and provides a bar graph displaying example data comparing the frequency of TR1 cells in the spleen as determined by % of CD4+ FoxP3−.
Figure 1I:
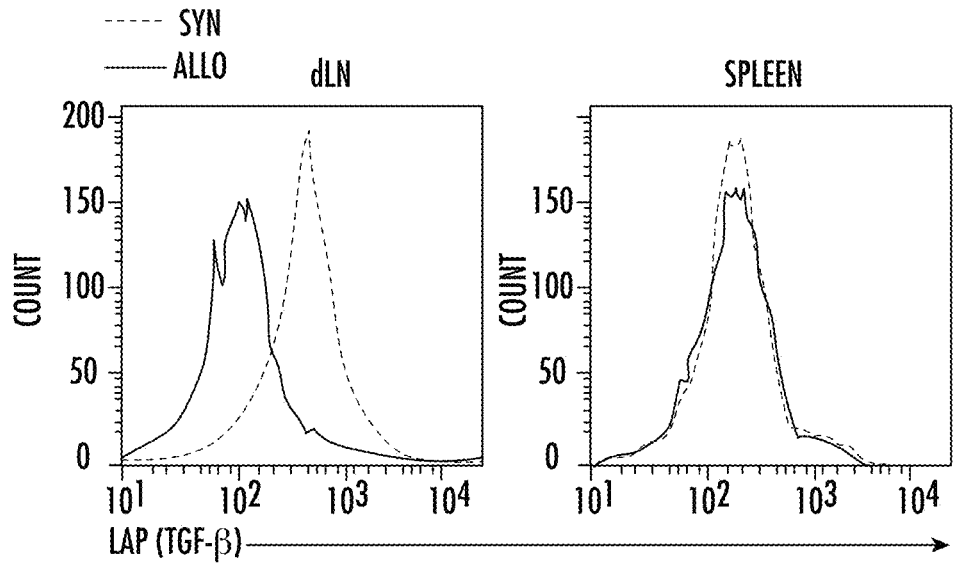
FIG. 1I illustrates overlaid histograms gated on CD4+ FoxP3+ cells, displaying LAP expression.
Figure 1J:
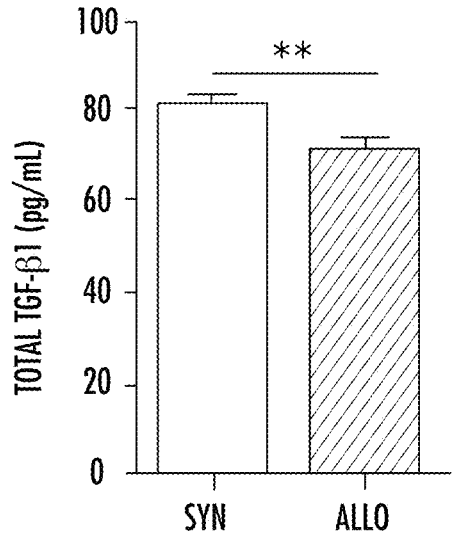
FIG. 1J presents enzyme-linked immunosorbent assay of total transforming growth factor-beta1 (TGF-$\beta$1) in the serum of subjects on the day of sacrifice. In the date for the figures, n=12 (syngeneic) or 18 (allogeneic) mice per group. Data for FIGS. 1A-1J are presented as mean±SEM of three independent experiments. *P<0.05, P<0.01, **P<0.0001 by Student's t-test.

T regulatory cells (Treg) play a critical role in tolerance and the decrease in their functions is associated with strong inflammation. To investigate the potential mechanisms that dampen the basal Treg induction during an immune response, an allogeneic skin-graft model of transplantation was used. To that end, C57BL/6 mice (H-2b, BL6), were given age- and sex-matched syngeneic (syn) (BL6) or allogenic (allo) C3H (H-2k, C3H) full-thickness ~1×1 cm2 tail skin transplants on the dorsal lateral surface. Ten days after transplantation, mice were sacrificed, and their draining lymph nodes (dLN) and spleens were harvested and assessed for the type and frequency of Tregs present. The main Treg subtypes investigated in the study: natural Tregs (nTregs), that are demarcated by surface CD4+ and Neuropilin-1 (Nrp1) expression and express the transcription factor FoxP3, peripheral Tregs (pTregs) that are CD4+, FoxP3+, Nrp1−, or Nrp1LO; and Tr1 T cells, which are CD4+, FoxP3 CD25−, CD49b+, Lag-3+ (CD223+), and express inducible T-cell costimulatory (ICOS). In addition, these cells express higher latent-associated TGF-β and secrete IL-10. In the dLN of allografted mice, but not in the spleen, there was a significant reduction in the percentage of nTregs and pTregs when compared to syngrafted mice (FIG. 1A-FIG. 1E). In contrast, there were no significant changes in the percentages of Tr1 cells (FIG. 1F-FIG. 1H). Additionally, when looking at the amount of latent-associated peptide—TGF-β1 (LAP) on CD4+ FoxP3+ cells, a notable decrease in the percentages of these Tregs in the allograft dLN (FIG. 1I) was observed. Due to the requirement of TGF-β1 for pTreg induction, and the decrease in LAP on Tregs after allotransplantation, TGF-β1 levels in the serum were measured on the day the mice were euthanized and it was found that the presence of TGF-β1 was diminished after allotransplantation as well (FIG. 1J).

A miRNA Cluster is Altered in dLN CD4+ Cells

Figure 2A:
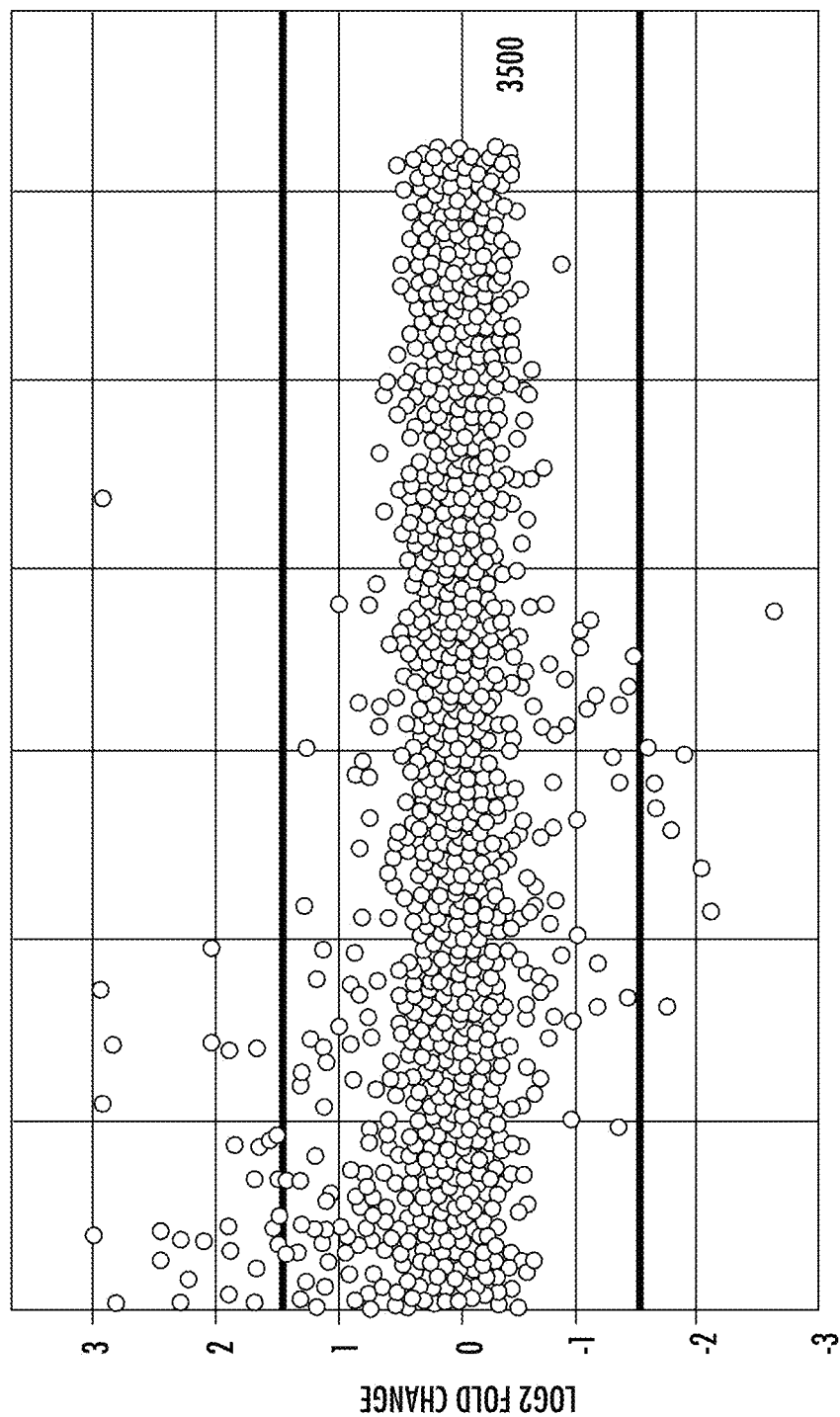
FIG. 2A illustrates a dot plot of all miRNAs and their associated fold change from an array of miRNA isolated from CD4+ T cells from naïve mice or from the dLN of mice receiving syn- or allograft 10 days post-transplant. Data analyzed as miRNA from the allotransplant group that were differently regulated from the naïve and syn-groups, but did not overlap with changes occurring between the naïve and syn-group. The lines indicate a log 2 fold change of 1.5, and only miRNAs with an up- or downregulation >1.5 log 2 fold change were considered for analysis.
Figure 2B:
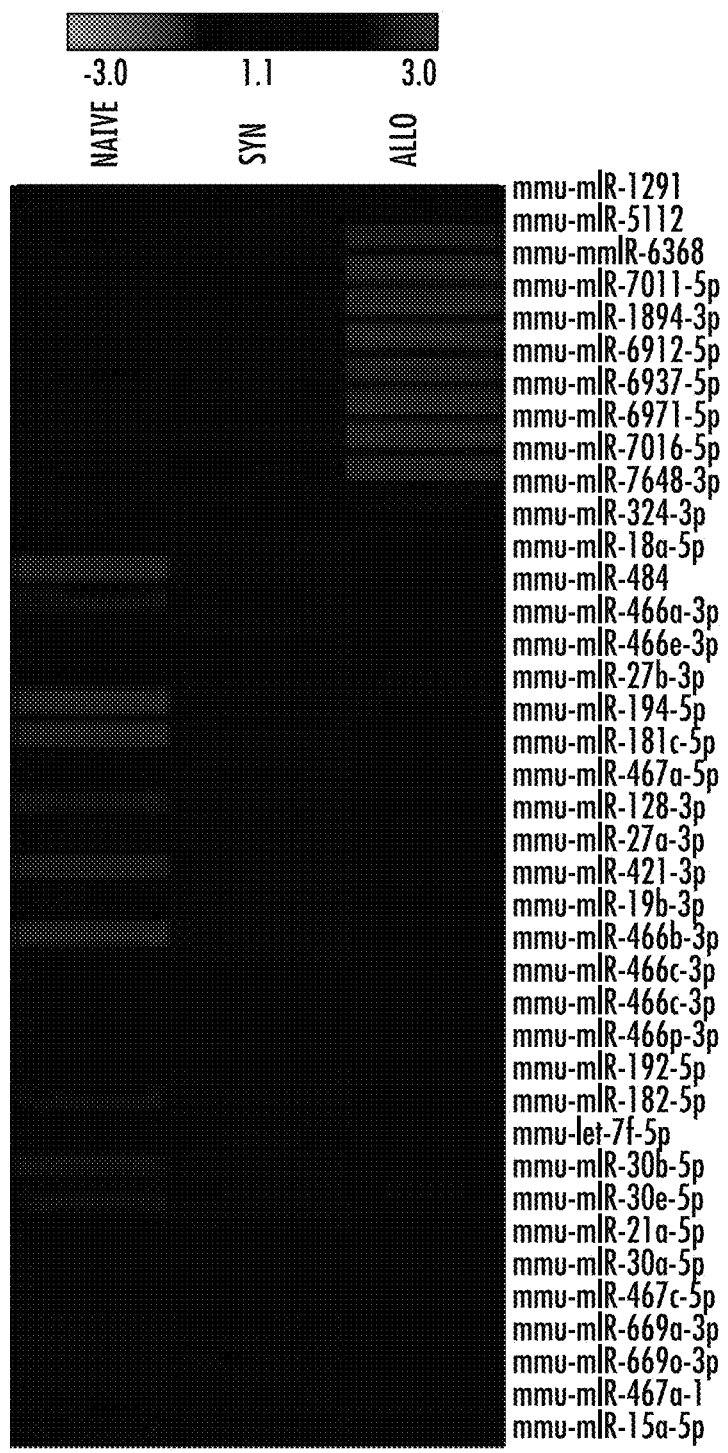
FIG. 2B is a heatmap representing miRNAs of the array of FIG. 2A with a >1.5 log 2 fold change between allo and syn/naïve groups in CD4+ T cells.
Figure 2C:
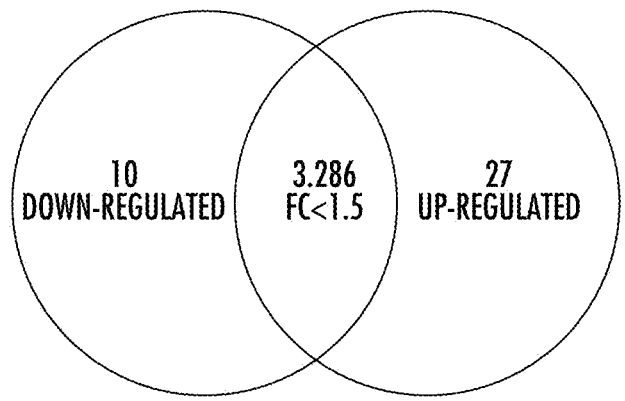
FIG. 2C illustrates a Venn Diagram that was constructed to depict the number of up- and downregulated miRNAs of the array of FIG. 2A that were ≥1.5-fold change after alloantigen exposure.

It was also investigated if changes in Tregs were associated with alterations in miRNA expression because miRNA are known to regulate T cell differentiation and plasticity. To that end, a miRNA expression microarray was performed using RNA isolated from purified CD4+ T cells from the dLNs of syn- or allografted mice and were compared to similar analysis from naïve lymph node CD4+ T cells. A dot plot was constructed to display the differential fold change expression of 3,164 miRNAs between the syn and allo groups; the red lines indicate a fold change of 1.5 in either direction (FIG. 2A). A heatmap was constructed of all the miRNA from the array that displayed a 1.5 or greater fold change in the allo group compared to both the naïve and syn groups (FIG. 2B). A Venn diagram was constructed to highlight the miRNAs that displayed at least a 1.5-fold change between the syn and allo groups (FIG. 2C). A compelling finding was that 10 of the 27 miRNAs that were found to be upregulated in the allo group (compared to both naïve and syn groups) all came from the same cluster of miRNA that was contained in the $10^{th}$ intron of the Polycomb group gene Sex combs on the midleg with four MBT domains-2 (Sfmbt2) on mouse chromosome 2, henceforth referred to as Chromosome 2 miRNA cluster (C2MC) (Table 2). C2MC has also been referred to as the miR-297-669 cluster.

TABLE 2

Upregulated miRNAs from microarray in the allo group and the 943 associated fold change.

| Transcript ID | Array Fold Change |
| --- | --- |
| Mmu-miR-466a-3p | 1.63 |
| Mmu-miR-466e-3p | 1.63 |
| Mmu-miR-467a-5p | 1.86 |
| Mmu-miR-466b-3p | 2.03 |
| Mmu-miR-466c-3p | 2.03 |
| Mmu-miR-466p-3p | 2.03 |
| Mmu-miR-669a-3p | 2.96 |
| Mmu-miR-466o-3p | 2.96 |
| Mmu-miR-467a-5p | 2.96 |

Validation of miR-466a Expression and Predicted mRNA Targeting

Figure 3A:
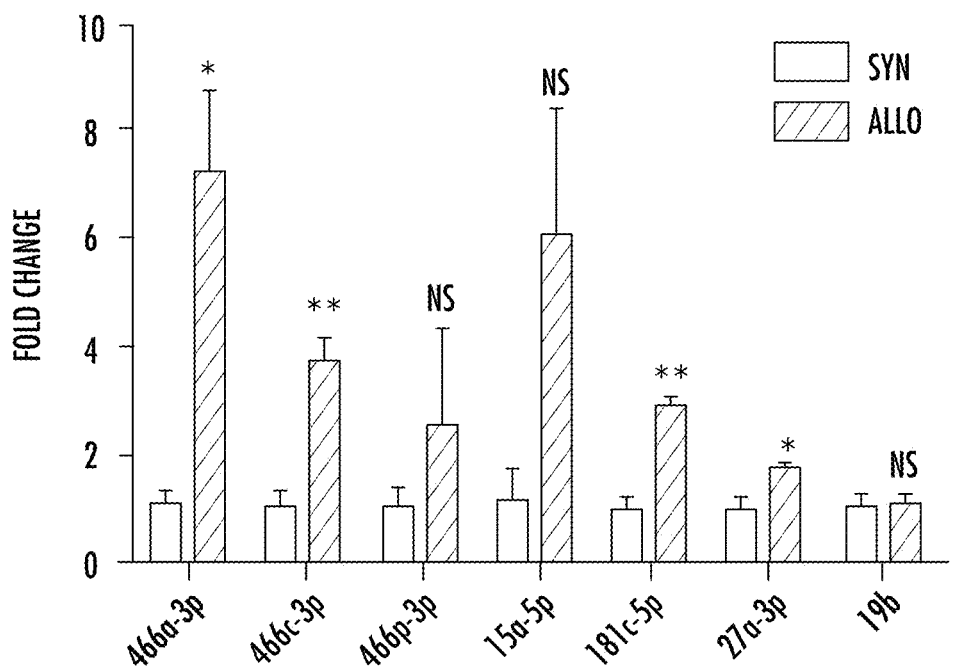
FIG. 3A illustrates a bar graph displaying example data demonstrating validation of microarray results through quantitative real-time (aRT)-PCR. Results demonstrate that alloantigen-induced microRNAs (miRNAs) target transforming growth factor-beta (TGF-β) family members and signaling molecules. Total RNA was extracted from purified CD4+ cells in the draining lymph node (dLN) of syn- or allografted mice 10 days post-transplant.
Figure 3B:
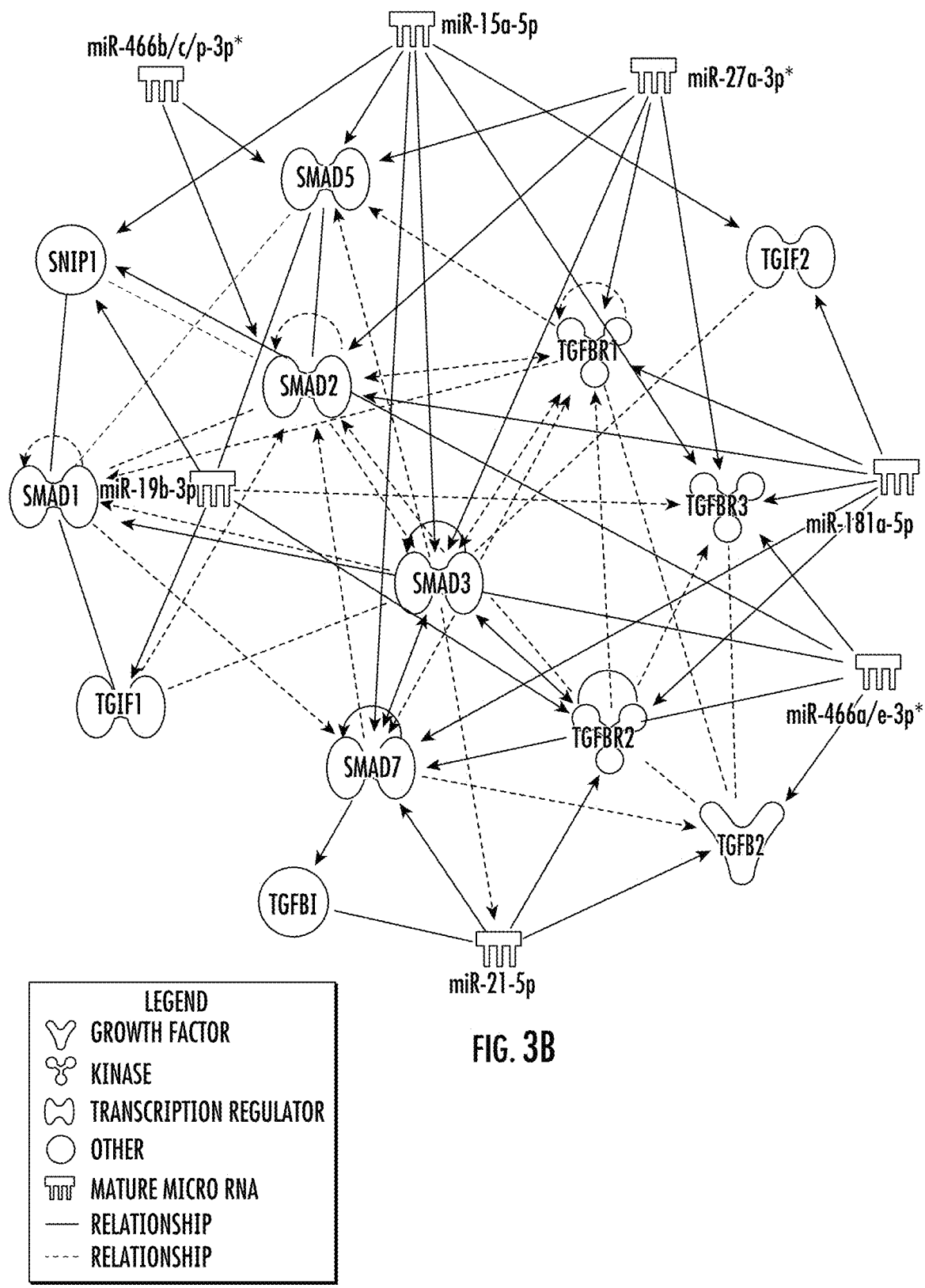
FIG. 3B illustrates an Ingenuity Pathway Analysis of micro-RNA of FIG. 3A and predicted gene targets.
Figure 3C:
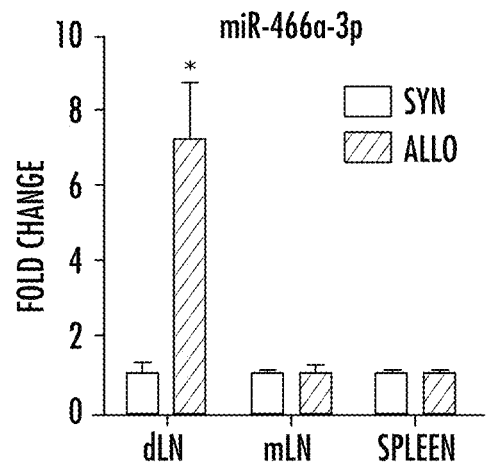
FIG. 3C presents fold change miR-466a expression in the dLN, spleen, or mesenteric lymph node (mLN) of purified CD4+ cells derived from syn- or allografted mice.
Figure 3D:
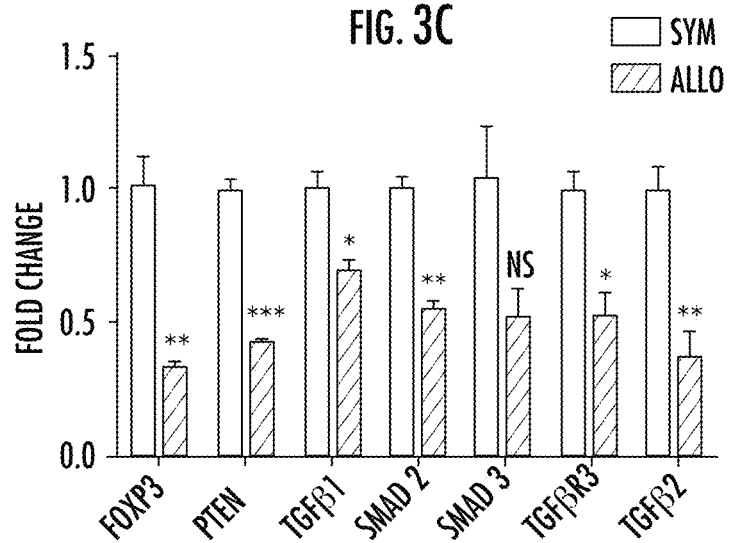
FIG. 3D presents qRT-PCR validation of mRNA expression changes in the dLN CD4+ cells of syn- or allografted mice; n=8 (syngeneic) or 12 (allogeneic) mice per group.
Figure 3E:
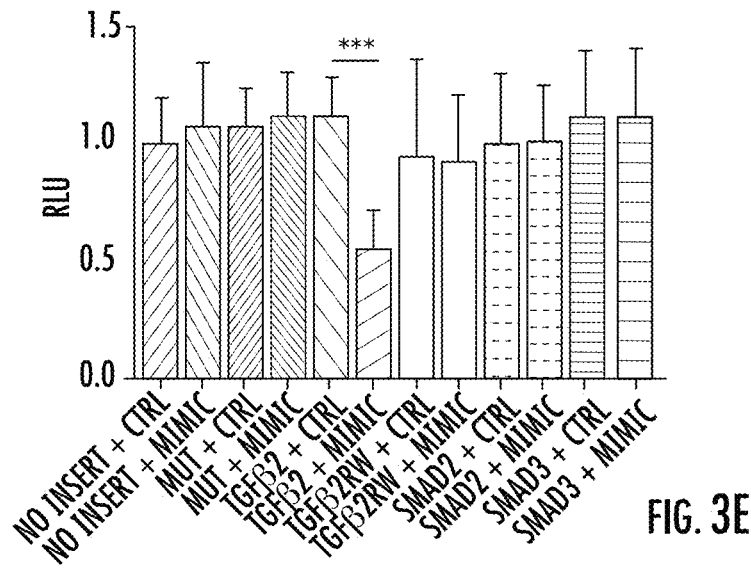
FIG. 3E presents the relative luciferase expression in EL-4 cells transfected with luciferase reporter constructs which contained 3' untranslated region (3'UTR) of proteins of interest or a mutated 3'UTR, together with miR-466a-3p mimics or the negative scramble control. A total of 48 hours after transfection, luciferase activity was detected. Normalized data of FIGS. 3A-3C were calculated as the quotient of Renilla/firefly luciferase activities and are presented as mean±SEM of three independent experiments with two technical replicates indicating six measurements. *P<0.05, P<0.01, *P<0.005, ****P<0.0001 by Student's t-test.

Expression of these miRNA was validated using qRT-PCR (FIG. 3A). Using Ingenuity Pathway Analysis (IPA) and microrna.org, several of the miRNA that were upregulated after allografting were found to target many members in the family of TGF-β signaling (FIG. 3B), consistent with a clear role for TGF-β1 in the differentiation of naïve CD4+ T cells into pTregs and tolerance. Data demonstrating a decrease in pTregs, LAP+ Tregs, and circulating TGF-β1 (FIGS. 1A, 1D, 1I, 1J) indicated that the TGF-β1 pathway may be attenuated after allotransplantation, an avenue that was further pursued. Among the upregulated miRNAs, the specific miRNA from C2MC with the highest validated expression in CD4+ T cells draining from the allograft was miR-466a-3p (FIG. 3A), henceforth referred to as miR-466a. This miRNA was chosen as the main miRNA of interest, both because of its noteworthy upregulation (FIG. 3A) and because its seed sequence is identical to miR-297 (a/b/c)-3p, miR-446d-3p, miR-467g, and miR-669d-3p, other members of C2MC. Upregulation of miR-466a after allotransplantation was specific to dLN CD4+ cells, as it was not significantly altered in splenic CD4+ cells or other peripheral LN CD4+ cells (FIG. 3C). Predicted targets of C2MC in (FIG. 3B) were validated through qRT-PCR (FIG. 3D) to be down-regulated in allograft dLN CD4+ cells. The mRNA targeted by miR-466a were also investigated. Predicted target, binding, and miRSVR score of miR-466a—mRNA interactions are displayed in a table (FIG. 9). The 3'-untranslated region (3' UTR) was cloned for several mRNA of interest (Smad2, Smad3, TGF-β2 and TGF-βR3), as well as a mutated 3' UTR, immediately downstream of luciferase in a luciferase reporter assay. EL-4 cells were transfected with the luciferase reporters or a control vector lacking any 3' UTR inserts in the presence of either a miR-466a mimic or a scramble control. It was noted that in the presence of miR-466a mimic, the luciferase activity of the reporter with the TGF-β2 3' UTR cloned into its sequence was significantly lower, while such a decrease was not seen in the presence of the scramble control, any of the other cloned 3' UTRs, or in the mutated control group (FIG. 3E). This finding was consistent with the predicted 7mer-m8 seed match shared between miR-466a and TGF-β2.

miR-466a Targets Treg Polarization Through TGF-β2

Figure 4A:
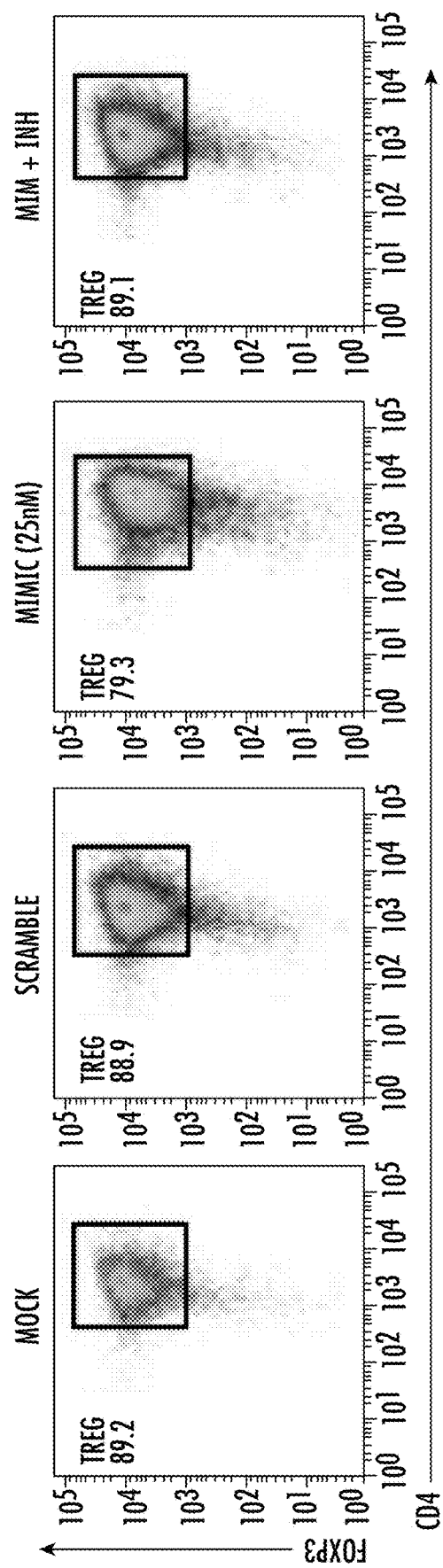
FIG. 4A presents dot plots gated on CD25HI cells and supporting the finding that miRNA 466a-3p transfection inhibits regulatory T cell (Treg) polarization. Purified naïve CD4+ T cells were cultured under Treg-polarizing conditions along with the indicated mimic, control, or inhibitor conditions. Cells were harvested 48 hours after addition of cytokines and miRNA mimics, inhibitors, or controls and subject to flow cytometry, immunoblot and quantitative real-time-PCR.
Figure 4B:
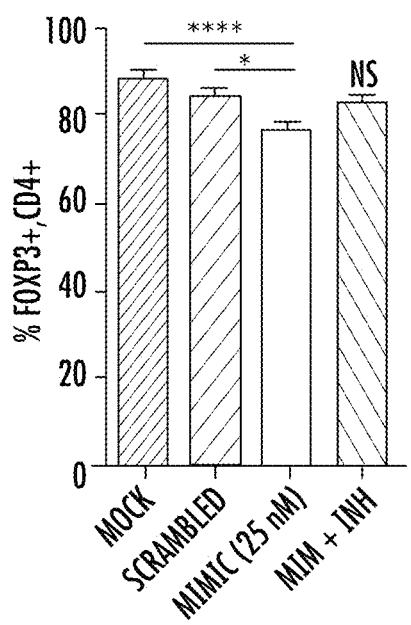
FIG. 4B presents quantification of data of FIG. 4A.
Figure 4C:
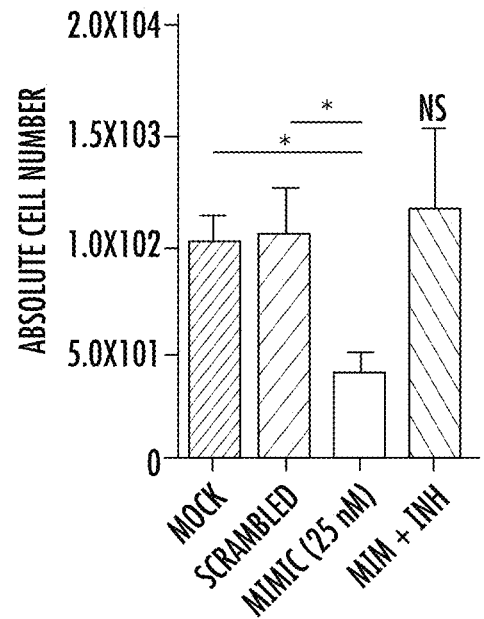
FIG. 4C presents additional quantification of data of FIG. 4A
Figure 4D:
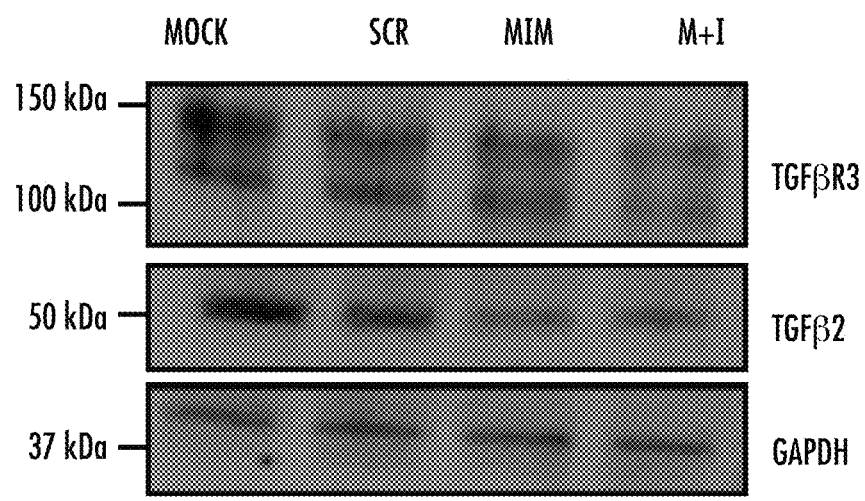
FIG. 4D illustrates a representative immunoblot assay showing protein expression for TGFBR3, TGFB2, and GAPDH.
Figure 4E:
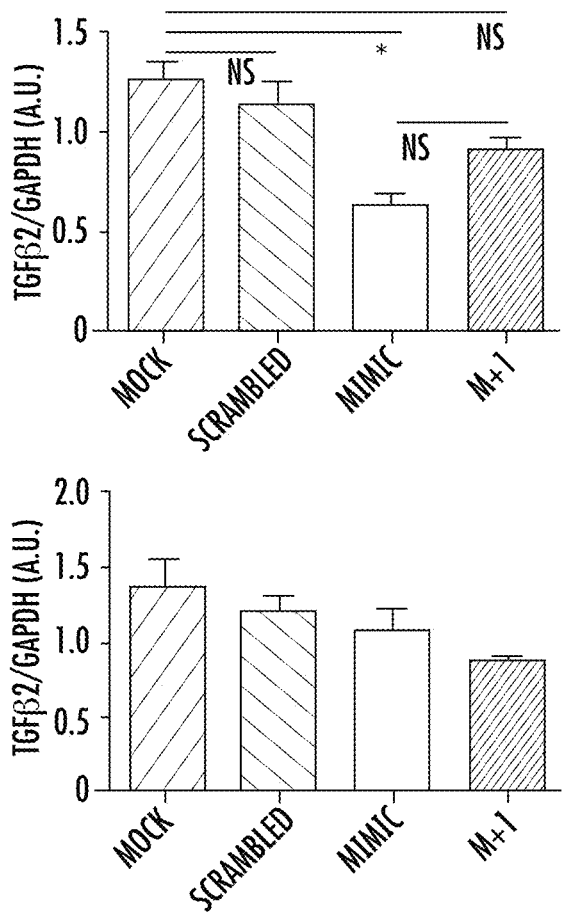
FIG. 4E presents associated densitometric measurements of transforming growth factor-beta 2 (TGF-β2) and TGF-βR3 (alternatively presented as TGFBR3).
Figure 4F:
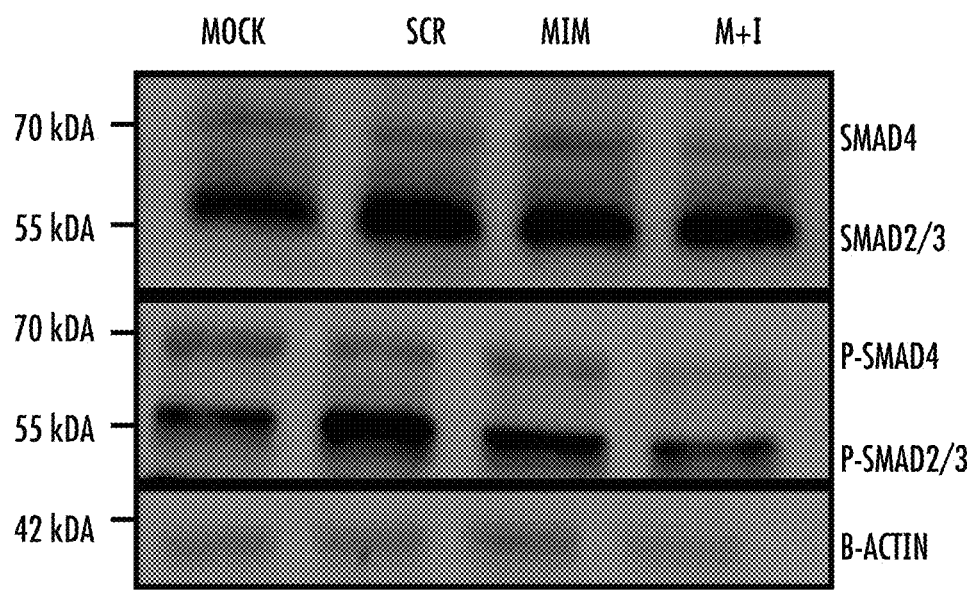
FIG. 4F illustrates an immunoblot assay showing protein expression for Smad4, Smad2/3, P-Smad4, P-Smad2/3, and B-actin.
Figure 4G:
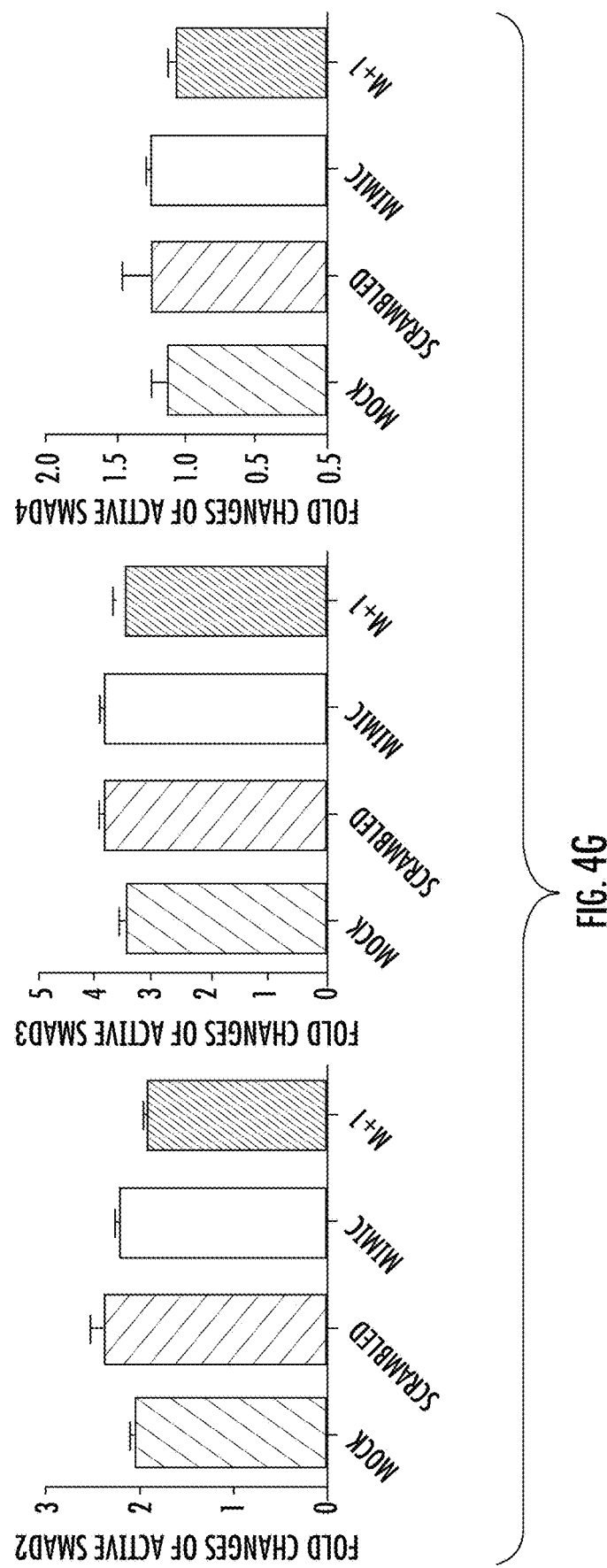
FIG. 4G illustrates bar graphs displaying quantification of activated Smad 2, 3, and 4.

To directly test the role of miR-466a on Treg differentiation, an in vitro Treg polarization model was used. To that end, purified naïve CD4+ T cells cultured with cytokines were transfected with either mock (empty vector), scramble control (25 nM), mimic (25 nM), or mimic+inhibitor (100 nM). The data showed that transfection with mimic, but not any of the other conditions, could suppress the generation of Tregs, as demarcated by the co-expression of CD4 and FoxP3 (FIG. 4A-FIG. 4C). It was worth noting that the mimic caused a robust decrease in the total number of Tregs generated in culture when compared to controls (FIG. 4 C). Transfection efficiency was validated with qRT-PCR. The mRNA and protein levels of the predicted targets of miR-466a were quantified after transfection, and the results indicated that the mRNA expression of Smad2, Smad3, TGF-β1, TGF-β2, and TGF-βR3 were reduced after mimic transfection compared to the other conditions. However, upon examining the protein level, although both Smad2 and Smad3 showed active phosphorylation, as is to be expected upon TGF-signaling, the only protein examined whose levels were decreased after mimic transfection was TGF-β2 (FIG. 4D-FIG. 4G). Continued Smad signaling despite the reduction in TGF-β2 is likely due to persistent signaling through TGF-β1. Additionally, there was a decrease in the amount of free-active TGF-β1 in the cells transfected with miR-466a mimic, and this alteration was reversed with the addition of the inhibitor.

Figure 4H:
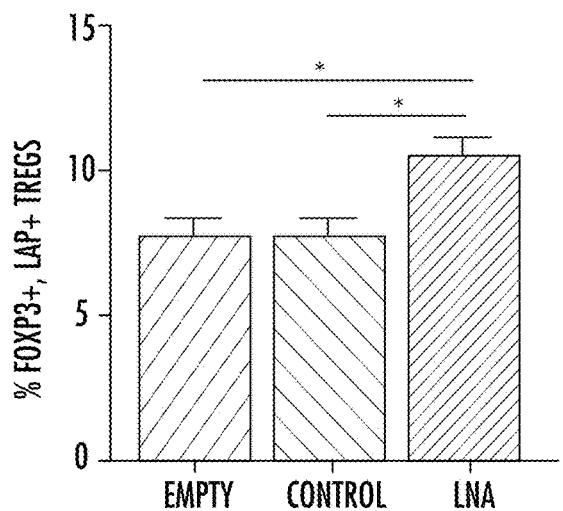
FIG. 4H quantification of flow cytometry data from LAP-expressing FoxP3 positive Treg cells after purified naïve CD4+ T cells were cultured with either TGF-β1 (5 ng/mL) or TGF-β2 (5 ng/mL), along with CD3 (3 μg/mL), CD28 (3 μg/mL), and IL-2 (5 ng/mL) for 5 days. CD4+ cells were purified from naïve mouse lymph nodes and stimulated ex vivo with CD3 (3 μg/mL) and CD28 (3 μg/mL) for 48 hours and administered Locked Nucleic Acid (LNA) or controls at the time of seeding.
Figure 4I:
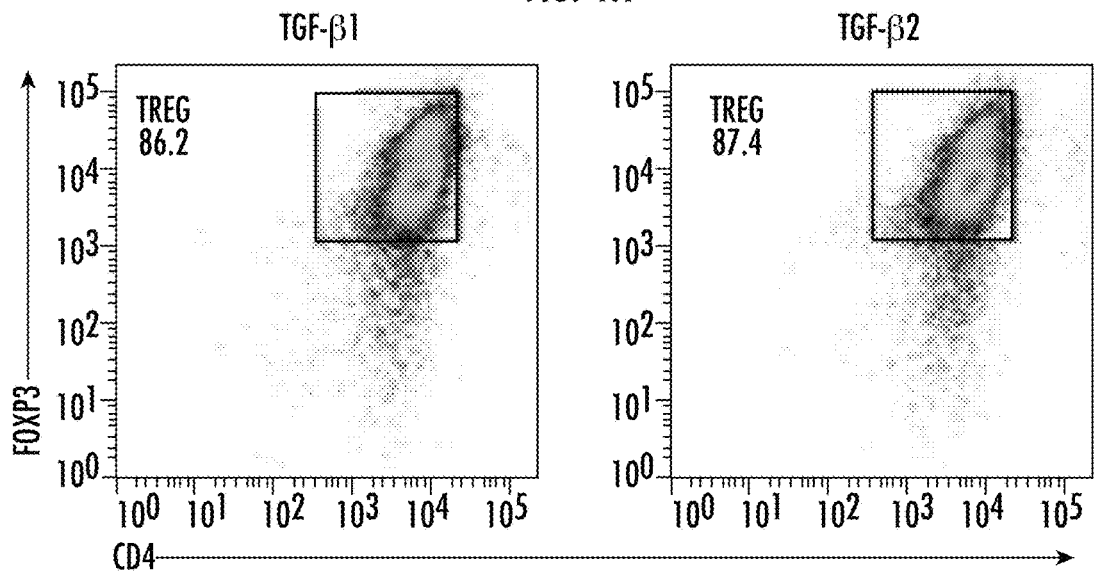
FIG. 4I illustrates representative flow cytometry dot of FoxP3, CD4-positive Tregs gated on CD25HI.
Figure 4J:
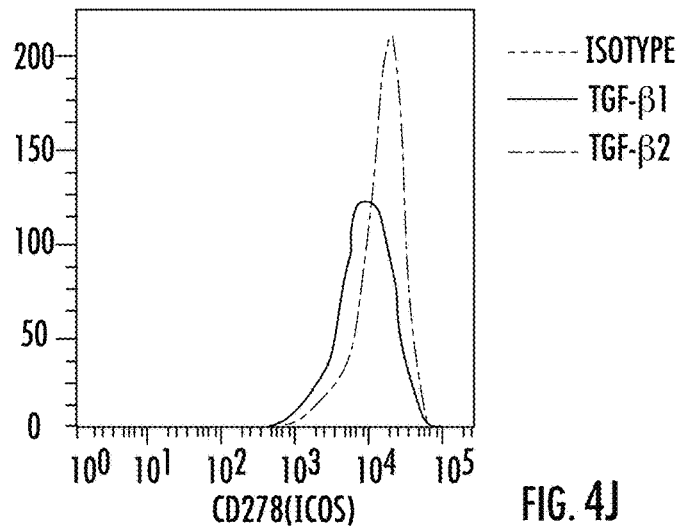
FIG. 4J illustrates a histogram showing their associated CD278 (ICOS) expression. Data of FIGS. 4A-4J are presented as mean±SEM of three independent transfection experiments. *P<0.05, P<0.005, **P<0.0001 by ANOVA with Tukey's multiple comparison test.
Figure 5A:
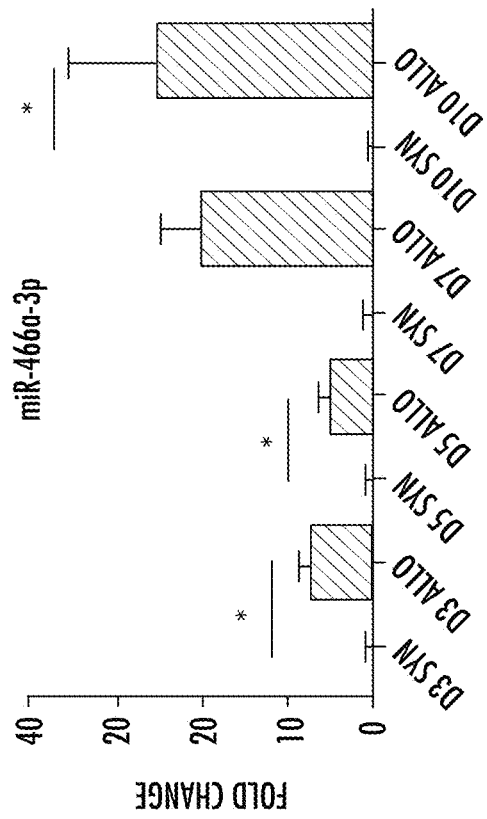
FIG. 5A demonstrates that co-culture of LN cells with alloantigen increased miR-466a-3p expression compared to LN cells cultured with syngeneic antigen at the indicated time points as determined by qRT-817 PCR. LN cells were administered alloantigen (50 μg/mL) for 10 days in complete media. Fresh media 818 and miRNA inhibitors or controls were added every 3 days. Cells were harvested and stained for Tc1, 819 Th1, Th17 and Treg cells.
Figure 5B:
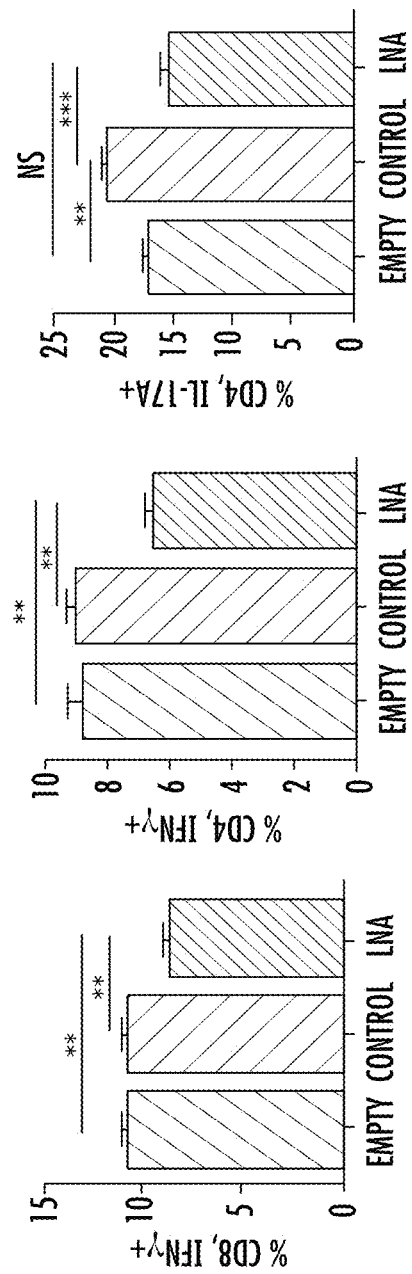
FIG. 5B presents quantitation of flow cytometry plots of data presented in FIG. 5A.
Figure 5C:
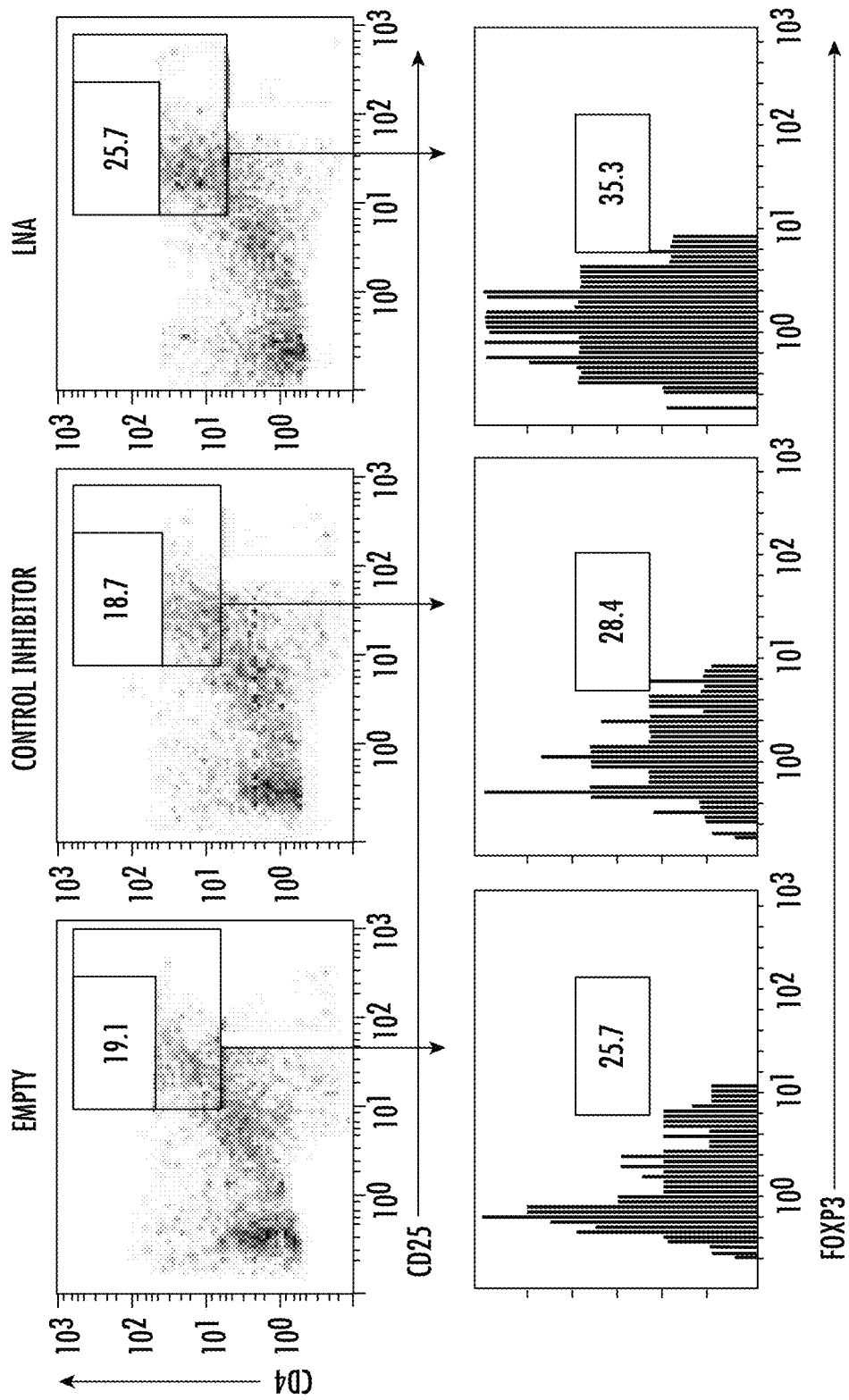
FIG. 5C illustrates histograms of FoxP3 expression (bottom row), gated on CD4+, CD25+ dot plots (top row).
Figure 5D:
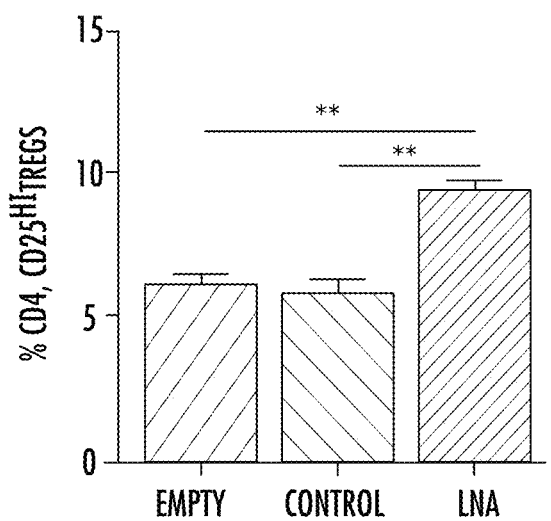
FIG. 5D illustrates quantification of data of FIG. 5C. Data of FIGS. 5A-5D are presented as mean 821±SEM of two independent transfection experiments indicating six measurements. *P<0.05, P<0.005, 822 *P<0.001, ****P<0.0001 by ANOVA with Tukey's multiple comparisons test.

The effect of miR-466a inhibition was also examined in a model having no exogenously administered TGF-β1. To that end, naïve CD4+ cells were purified and stimulated in vitro with anti-CD3/CD28 Ab in the presence of a locked nucleic acid (LNA) designed specifically to inhibit miR-466a/b/c/d/e/p-3p (referred to as LNA), or a control that was designed not to target any known miRNAs (control). Cells treated with LNA exhibited an increase in the number of CD4+ CD25HILAP+FoxP3+ Tregs compared to controls (FIG. 4H). To confirm that TGF-β2 can have a pronounced effect on Treg polarization, naïve CD4 cells were polarized with either TGF-β1 (5 ng/mL) or TGF-β2 (5 ng/mL). Both culture conditions induced the polarization of naïve T cells into Tregs, but TGF-β2-induced Tregs had increased expression of inducible T-cell costimulatory (ICOS), a marker of Treg fitness, compared to TGF-β1-induced Tregs (FIG. 4I).

miR-466a Inhibitor Decreases Pro-Inflammatory and Increases Anti-Inflammatory Cells after Co-Culture with Alloantigen To mimic more closely the in vivo environment of transplantation, an in vitro co-culture model was implemented wherein naïve LN cells were cultured with either syngeneic antigen or alloantigen (50 μg/mL). Co-culture with alloantigen provoked a robust increase in expression of miR-466a at several time points compared to cells cultured with syngeneic antigen (FIG. 5A). Next, LN cells were cocultured with alloantigen and LNA or control inhibitor and cells were analyzed by flow cytometry. LNA addition resulted in a decrease in pro-inflammatory T helper 1 (Th1) cells that were CD4+IFNγ+, cytotoxic effector CD8+ IFNγ+ cells (Tc1), and CD4+IL-17A+ T helper 17 (Th17) cells (FIG. 5B). In the same cultures, LNA also induced increased proportions of CD4+CD25HI FoxP3+ Tregs compared to controls (FIG. 5C-FIG. 5D).

LNA Attenuates Inflammatory Markers after Allogenic Skin Transplantation

Figure 6A:
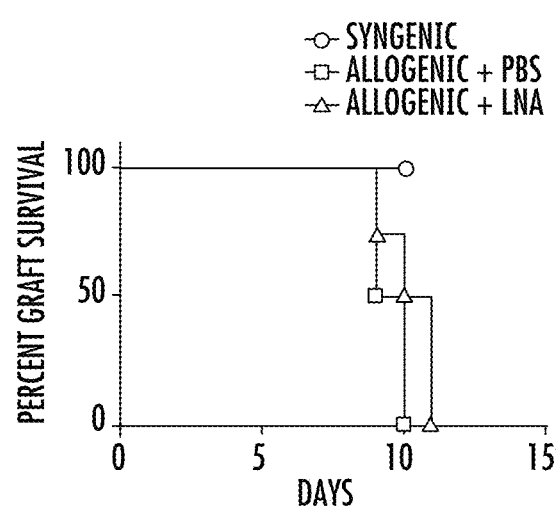
FIG. 6A presents a survival curve of mice receiving skin transplants and demonstrates that LNA mitigates dLN effector cell and cytokines. Female C57BL/6 830 mice were given either syn (BL6) or allo (C3H) tail skin grafts. Mice receiving allografts were given either LNA (10 mg/kg) or Vehicle i.p. 1 day before skin transplantation, and every 3rd day after that until termination of the study.
Figure 6B:
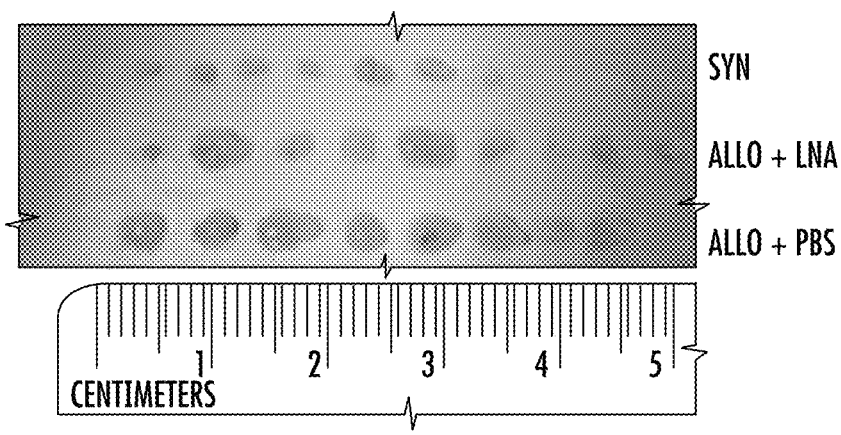
FIG. 6B illustrates an image of draining lymph nodes harvested twelve days after skin transplantation from indicated groups.
Figure 6C:
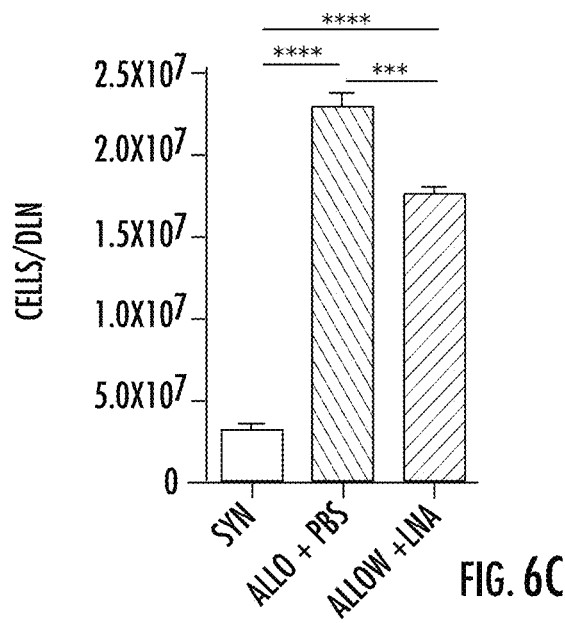
FIG. 6C presents the absolute cell count of the lymph nodes illustrated in FIG. 6B.
Figure 6D:
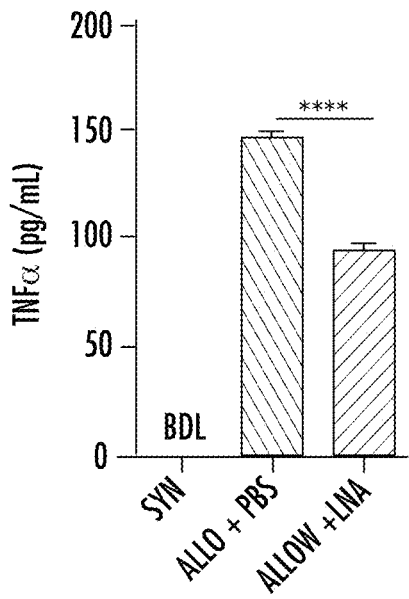
FIG. 6D presents ELISA results for TNFa from dLN cells following plating overnight in complete media and harvesting of culture supernatants.
Figure 6E:
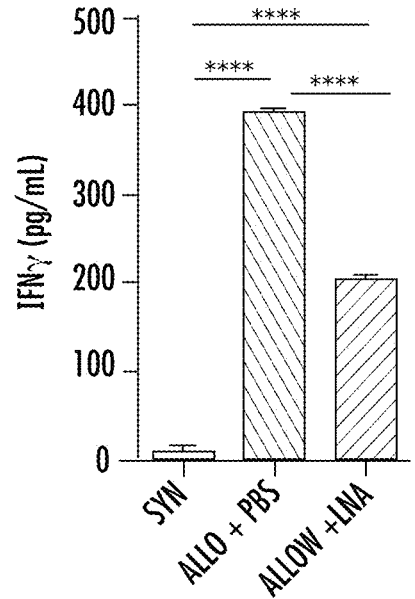
FIG. 6E presents ELISA results for IFNγ from dLN cells following plating overnight in complete media and harvesting of harvesting of culture supernatants.

Because LNA was effective in attenuating inflammatory T cells induced by alloantigen in vitro, its effect was investigated in vivo. To that end, C57BL/6 mice were given either C57BL/6 (syn) or C3H (allo) skin grafts and were administered LNA at a dose of 10 mg/kg starting 1 day before allografting, and every 3rd day thereafter, until termination of the study. While LNA caused a slight delay in allograft rejection, it was statistically not significant (FIG. 6A). However, mice given the allograft+LNA did exhibit significant decrease in the size and total cellularity of draining lymph nodes thereby indicating decreased host-versus-graft response and inflammation (FIG. 6B, FIG. 6C). In the same experiment, LNA failed to induce significant changes in the size and cellularity of the spleens, thereby demonstrating that LNA could be targeting the dLNs, the primary site of immune response against alloantigen, and the site of mir-466a upregulation. To determine if LNA-mediated effect on Tregs was having a functional impact on inflammatory cytokines, dLN cells harvested from LNA-treated mice were cultured overnight and the supernatants were examined for cytokines. The data showed that LNA derived cultures had significantly lower effector cytokines such as TNFα and IFNγ levels when compared to cells derived from allograft+Vehicle treated mice (FIG. 6D, FIG. 6E).

Figure 6F:
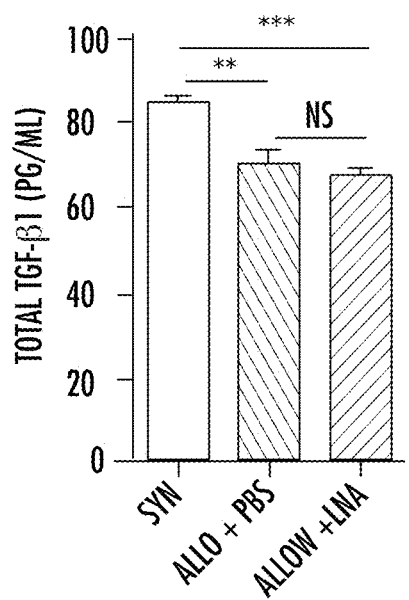
FIG. 6F presents ELISA results for TGF-β1 from serum taken upon sacrifice.
Figure 6G:
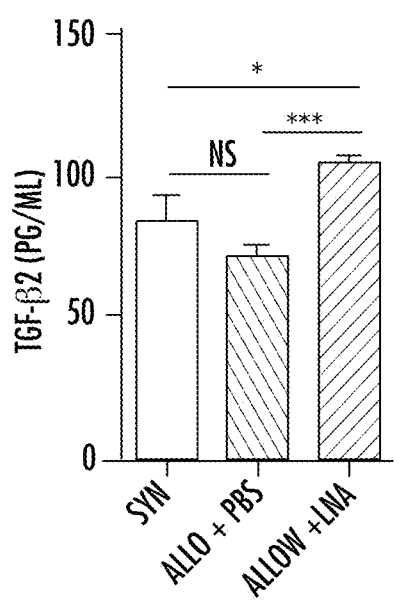
FIG. 6G presents ELISA results for TGF-β2 from serum taken upon sacrifice.

Mice receiving LNA exhibited no significant changes in the amounts of circulating TGF-β1; however, consistent with the ability of miR-466a to target TGF-β2, the LNA group demonstrated increases in circulating TGF-β2 when compared to syn or allograft+vehicle groups (FIG. 6F, FIG. 6G). Corroborating this finding, data showed an increase in the number of circulating memory Treg cells (FIG. 6H, FIG. 6I) in the LNA group, surpassing the number of memory Tregs in the syn group. When a histopathological analysis of the grafts was performed, results indicated that allograft+LNA mice showed a decrease in the levels of cellular infiltration and graft damage compared to allograft+vehicle controls (FIG. 6J).

LNA Reduces Intragraft Effector Cells and Cytokines

Figure 7A:
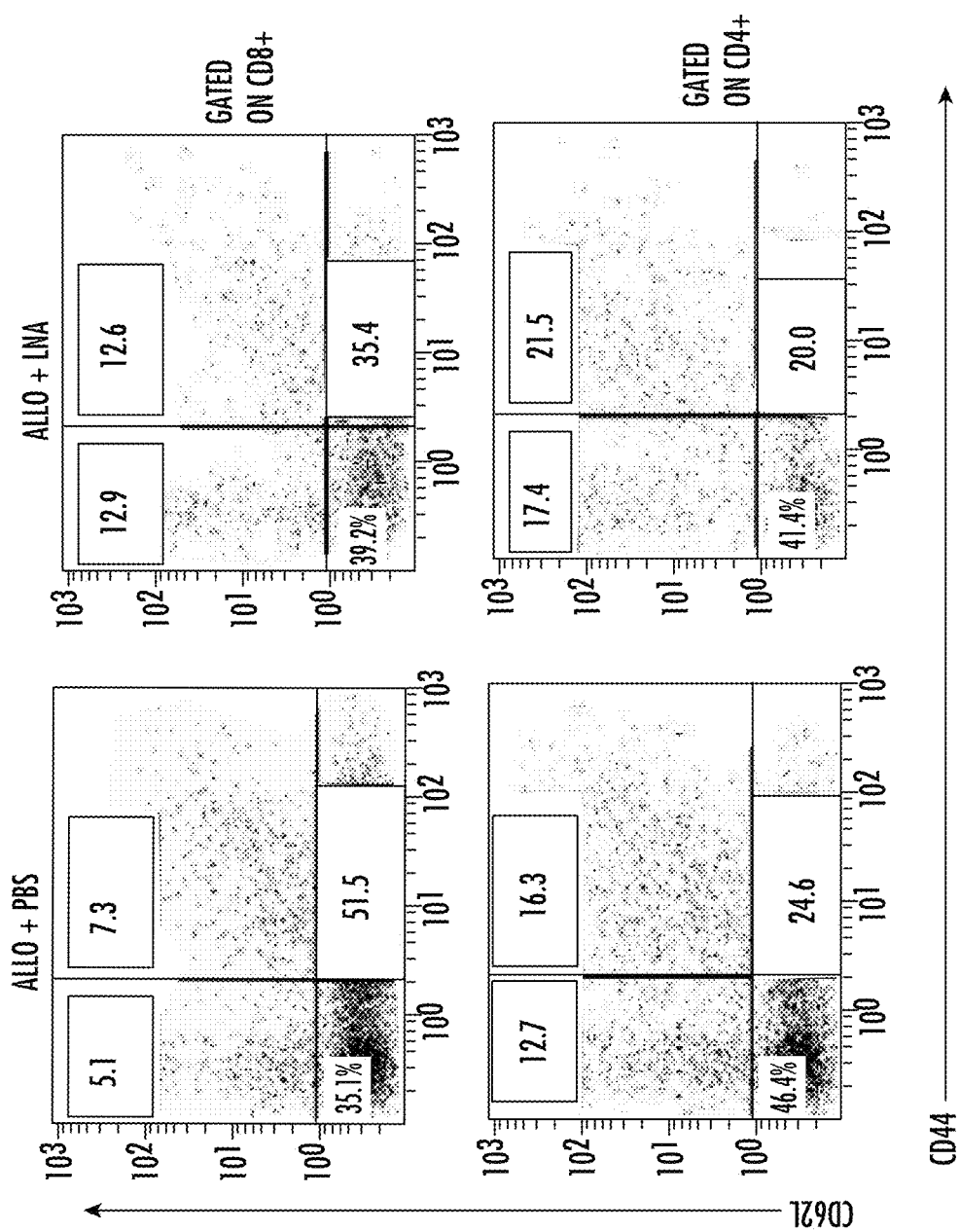
FIG. 7A representative dot plots displaying naïve (CD62LLow, CD44Neg), memory (CD62L+, CD44HI) and effector (CD62LLow, CD44HI) cell types gated on CD8 (upper row) and CD4 (lower row). Female C57BL/6 mice were given either syn (BL6) or allo (C3H) tail skin grafts. Mice receiving allografts were given either LNA (10 mg/kg) or PBS i.p. 1 day before skin transplantation, and every 3rd day after that until termination of the study. Upon rejection, grafts were aseptically excised, minced and digested to dislodge graft infiltrating cells (GICs). GICs were spun down, culture supernatants were collected, and live cells were used for flow cytometric analysis.
Figure 7B:
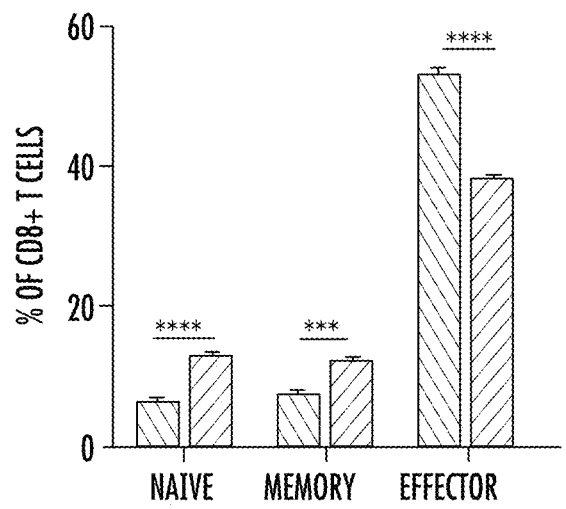
FIG. 7B presents the quantified percentages for CD8+.
Figure 7C:
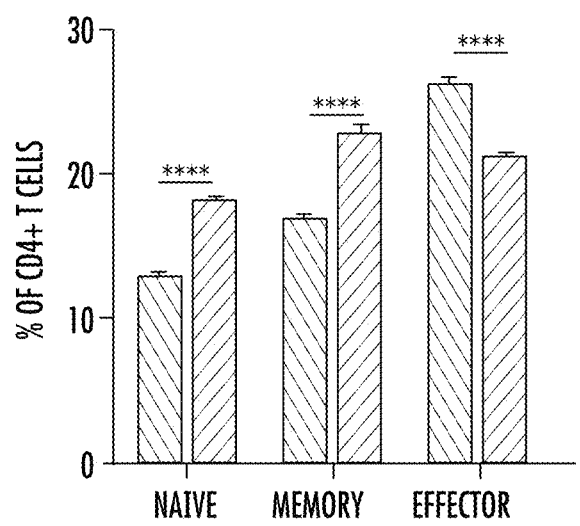
FIG. 7C presents the quantified percentages for CD4+.
Figure 7D:
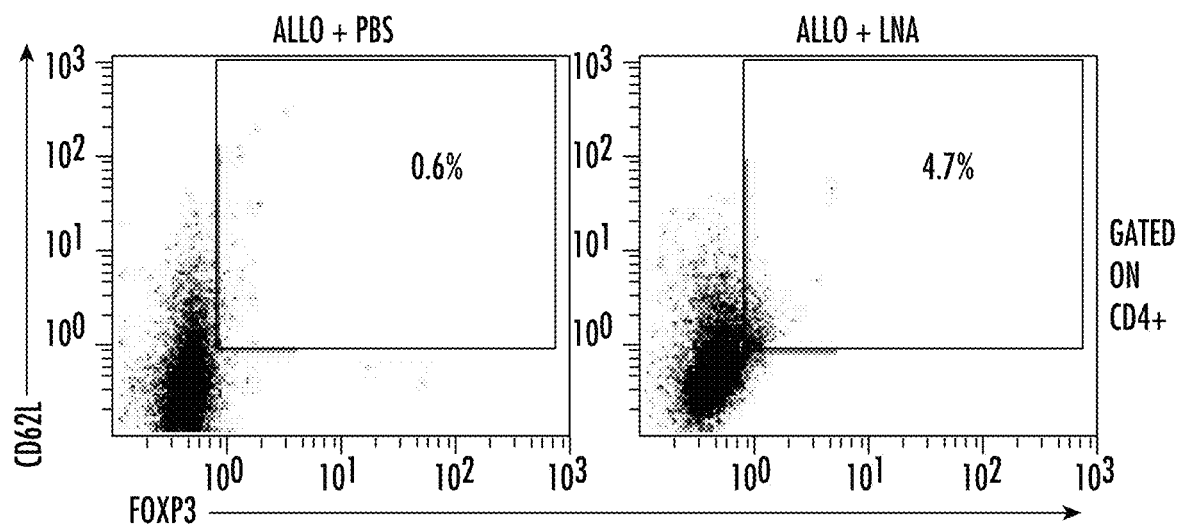
FIG. 7D presents dot plots of GICs double-positive for FoxP3 and CD62L, data were gated on CD4+ cells.
Figure 7E:
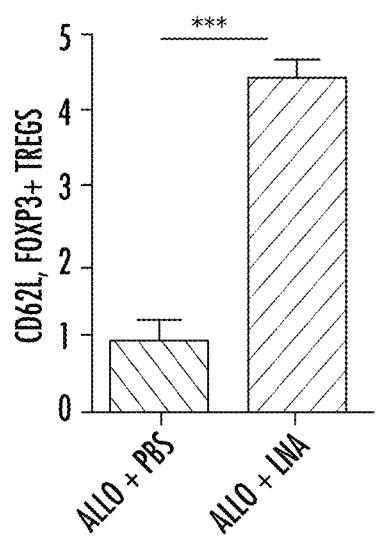
FIG. 7E presents quantification of data of FIG. 7D.
Figure 7F:
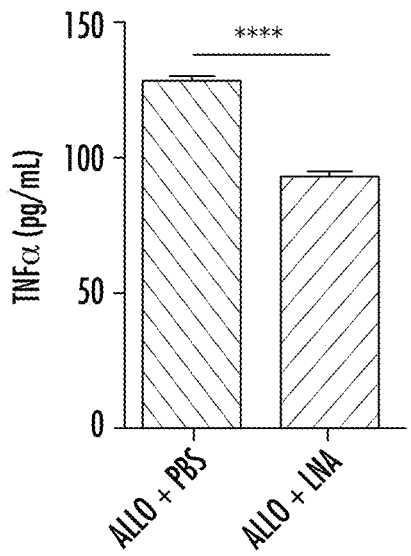
FIG. 7F presents ELISA results for the interrogation of effector cytokine TNFα from GIC supernatants.
Figure 7G:
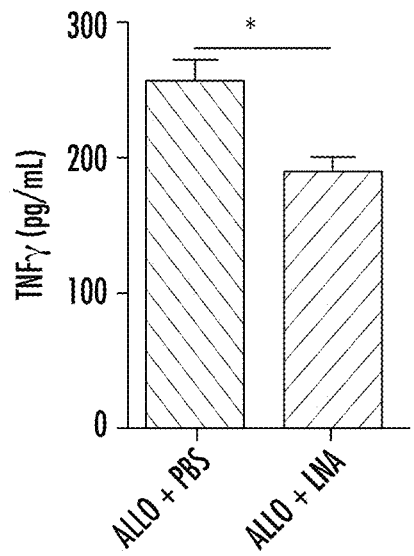
FIG. 7G presents ELISA results for the interrogation of effector cytokine IFNγ from GIC supernatants.
Figure 7H:
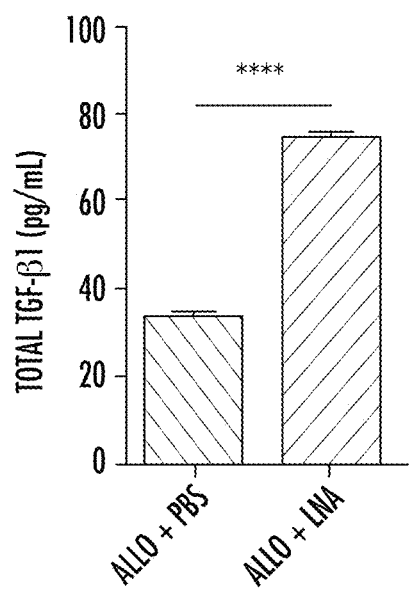
FIG. 7H presents ELISA results for the interrogation of anti-inflammatory cytokine TGF-β1 from GIC supernatants.
Figure 7I:
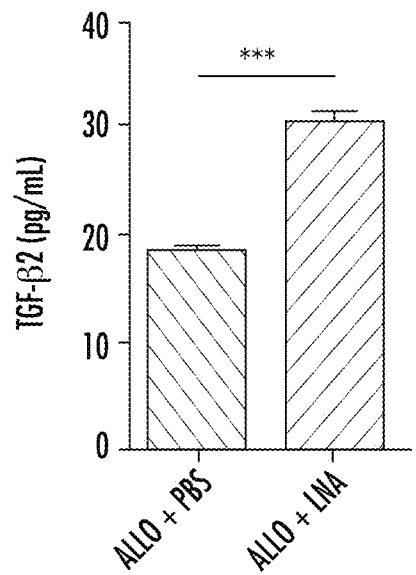
FIG. 7I presents ELISA results for the interrogation of anti-inflammatory cytokine TGF-β2 from GIC supernatants. Data of FIGS. 7A-7I are presented as mean±SEM; n=at least 4 per group. *P<0.05, P<0.005, *P<0.001, ****P<0.0001 by ANOVA with Tukey's multiple comparisons test or a Students t-test.

The nature of cells and cytokines seen within the graft after LNA or vehicle treatment was also studied. To that end, the grafts were excised, minced, and digested to retrieve graft infiltrating cells (GICs), which were either immediately stained or plated for 24 hours in complete media, to obtain GIC culture supernatants. The data revealed that LNA-treated animals had an increase in the percentage of naïve CD4+ or CD8+ GICs and a decrease in effector CD4+ or CD8+ GICs compared to the vehicle group (FIG. 7A-FIG. 7C). LNA treatment also resulted in an increase in the percentage of graft infiltrating CD4, CD62L, FoxP3+ Tregs, compared to the PBS group (FIG. 7D, FIG. 7E). Graft culture supernatants revealed that LNA treatment led to reduced levels of effector inflammatory cytokines, TNFα (FIG. 7F) and IFNγ (FIG. 7G), as well as increases in total TGF-β1 and TGF-β2 (FIG. 7H, FIG. 7I).

Figure 8F:
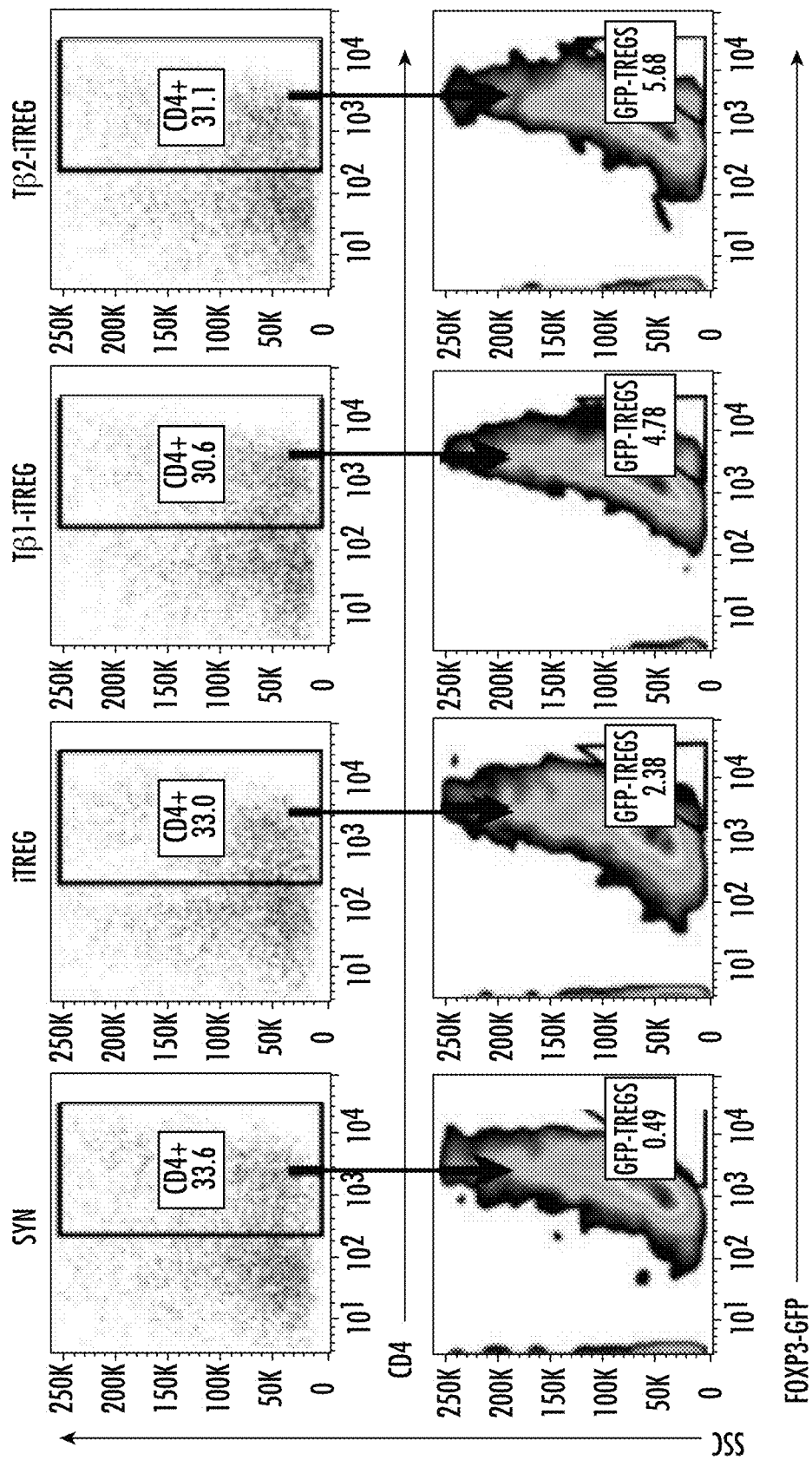
FIG. 8F illustrates flow cytometry plots (top) and corresponding density plots of GFP+, CD4+ co-expressing iTregs among graft infiltrating cells
Figure 8G:
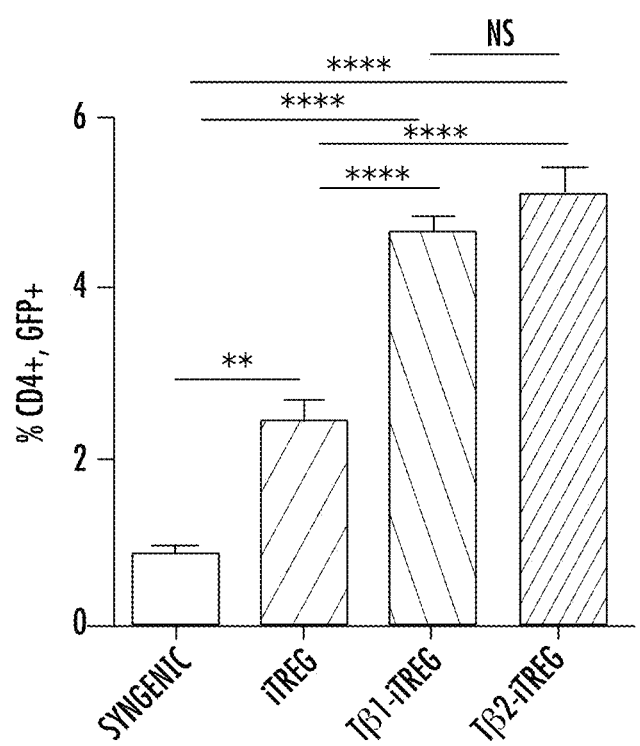
FIG. 8G illustrates a bar graph displaying quantified flow cytometry results.
Figure 8H:
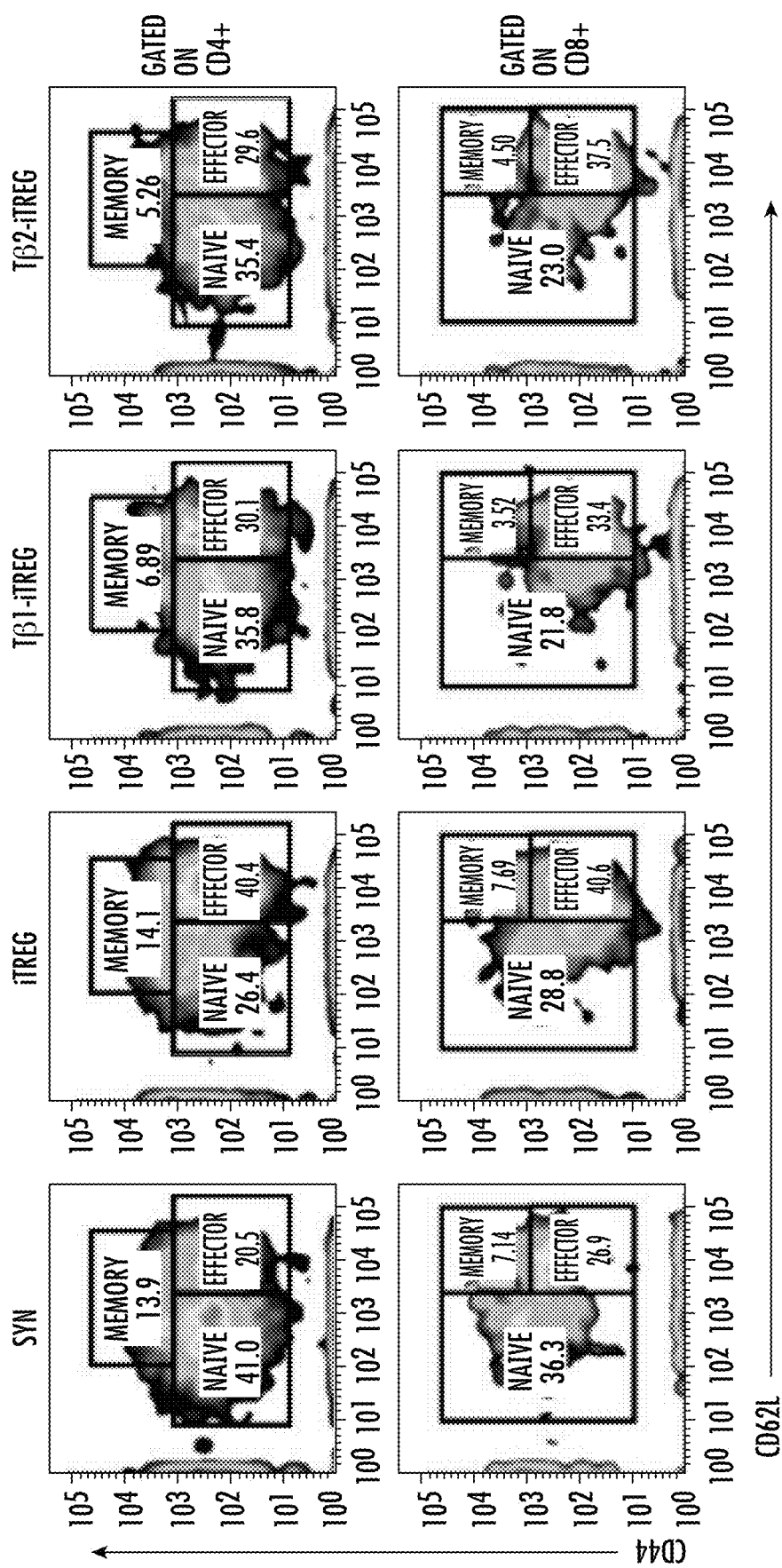
FIG. 8H illustrates density plots displaying graft infiltrating CD4+ and CD8+ naïve, memory and effector phenotypes.
Figure 8I:
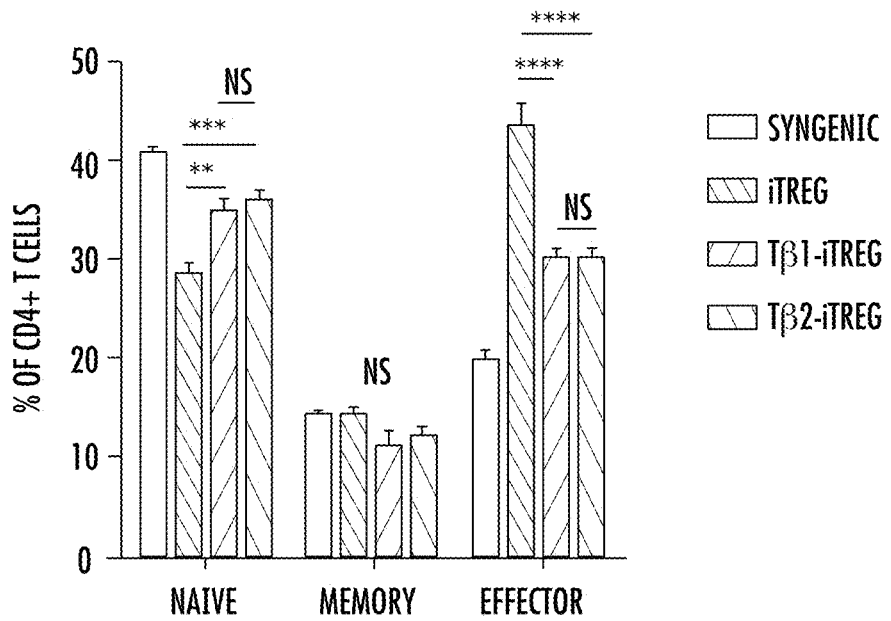
FIG. 8I illustrates a bar graph displaying quantified flow cytometry results.
Figure 8J:
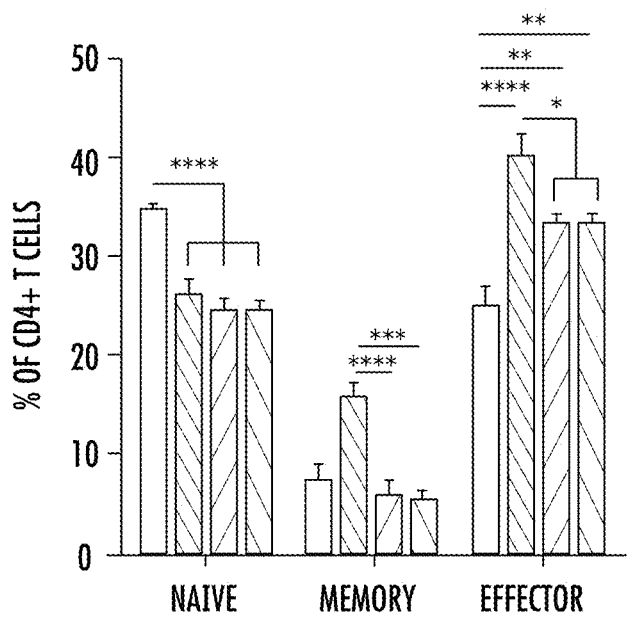
FIG. 8J illustrates a bar graphs displaying quantified flow cytometry results.
Figure 8K:
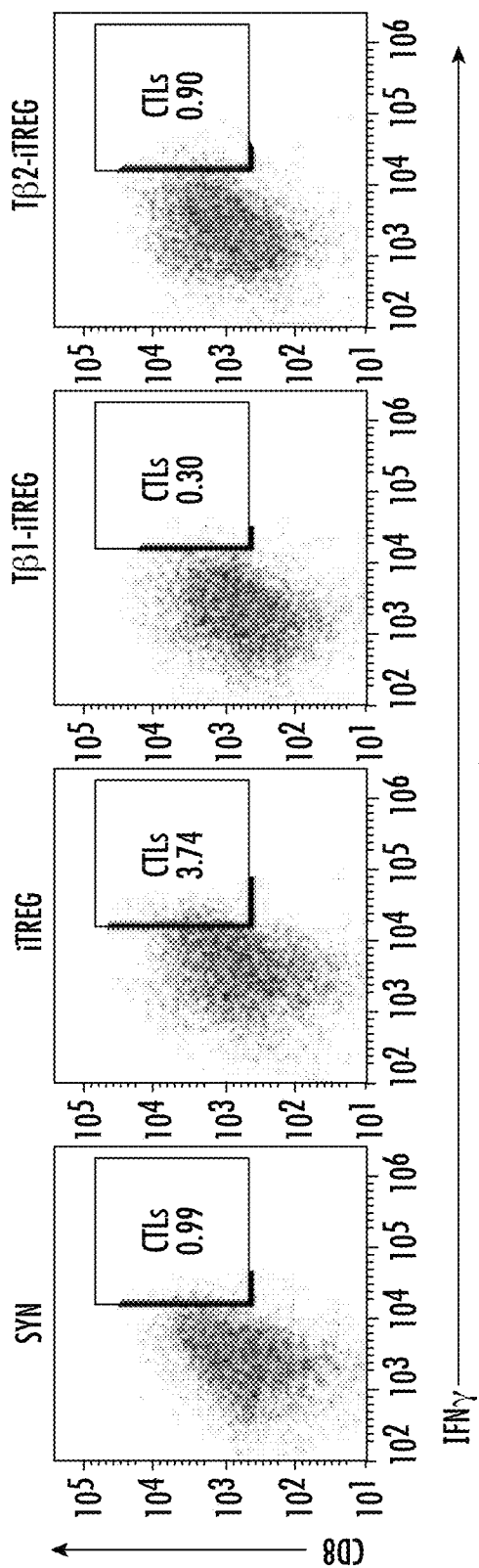
FIG. 8K illustrates flow cytometry plots displaying IFNγ and CD8+ CTLs.
Figure 8L:
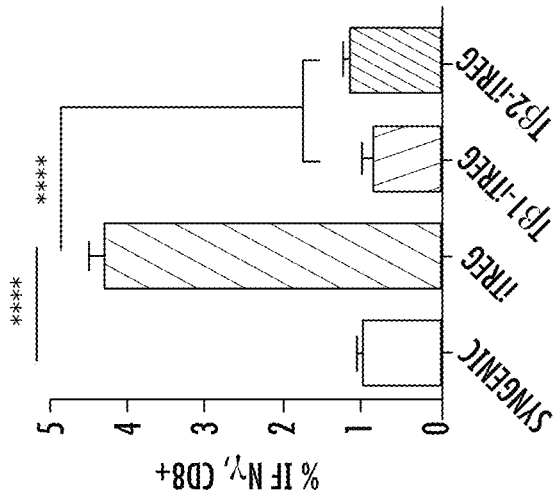
FIG. 8L illustrates a bar graph displaying quantified flow cytometry results. Data of FIGS. 8A-8J are presented as mean±SEM; n=at least 4 per group. *P<0.05, P<0.005, 939 *P<0.001, ****P<0.0001 by ANOVA with Tukey's multiple comparisons test, or a log-rank (Mantel-Cox) test for the survival curve.

TGF-β2-Induced Tregs are as Potent as TGF-β1-Induced Tregs in Attenuating Allograft Rejection Response To study the role of TGF-β2-induced Tregs in suppressing inflammation, CD4+ cells from C57BL/6 FoxP3GFP reporter mice were isolated and cultured with splenic APCs from allogenic mice, along with anti-CD3ε (10 μg/mL), anti-CD28 (4 μg/mL) and IL-2 (10 ng/mL). TGF-β1 is conventionally used to stimulate the production of both polyclonal and antigen-specific-induced Tregs (iTregs). The effect of culture with either TGF-β1 (5 ng/mL) or TGF-β2 (5 ng/mL) on iTreg generation was studied. Similar to the polarization findings in FIG. 4I, after 3 days of culture, data showed that TGF-β2 can induce the generation of iTregs (Tβ2-iTregs) to the same extent and phenotype as TGF-β1 (Tβ1-iTregs) (FIG. 8A, FIG. 8B). To test the efficacy of these cells at delaying acute rejection in vivo, after 3 days of co-culturing, iTregs were sorted for CD4+, FoxP3GFP co-expression, and $1 \times 10^6$ cells were intravenously injected into allograft recipient mice 1 day before skin transplantation. Syngeneic mice which did not receive any iTregs were used as controls. Tβ2-iTregs displayed potency equivalent to Tβ1-iTregs at delaying graft rejection (FIG. 8C), preventing graft destruction at a rate greater than iTregs generated without the addition of TGF-β1 or TGF-β2. iTregs were verified to be present in the dLN (FIG. 8D, FIG. 8E) to the same extent among all groups, although iTregs induced with TGF-β1 or TGF-β2 showed greater potential to home to the allograft (FIG. 8F, FIG. 8G). Indeed, grafts harvested 12 days after allotransplantation that were derived from mice administered Tβ1-iTregs and Tβ2-iTregs showed a decrease in graft infiltrating memory CD4+ cells (FIG. 8H, FIG. 8I), and a decrease in the number of graft infiltrating memory and effector CD8+ cells (FIG. 8H, FIG. 8J). In the periphery, Tβ1-iTregs and Tβ2-iTregs reduced circulating CD4+ and CD8+ cells displaying a memory phenotype but did not cause any change in circulating Tregs. Lastly, Tβ1-iTregs and Tβ2-iTregs could significantly reduce the number of graft infiltrating IFNγ-secreting CTLs compared to mice which received only iTregs (FIG. 8K, FIG. 8L).

While certain embodiments of the disclosed subject matter have been described using specific terms, such description is for illustrative purposes only, and it is to be understood that changes and variations may be made without departing from the spirit or scope of the subject matter.

---

The invention claimed is:

1. A method for inducing a Treg phenotype in a plurality of naïve CD4+ T cells from a mammal, the method comprising:
   extracting the plurality of naïve CD4+ T cells from the mammal;
   culturing the plurality of naïve CD4+ T cells with Cd11c+ allogenic antigen presenting cells; and
   further culturing the plurality of naïve CD4+ T cells with TGFβ2, the concentration of the TGFβ2 being between 0.5 ng/mL to 40 ng/mL; wherein upon the further culturing, a Treg phenotype is induced in the plurality of naïve CD4+ T cells.

2. The method of claim 1, comprising further culturing the plurality of naïve CD4+ T cells with one or more compounds selected from the group consisting of: anti-CD3e, anti-CD3g, anti-CD3d, and IL-2.

3. The method of claim 2, comprising further culturing the plurality of naïve CD4+ T cells with an anti-CD28 antibody.

4. The method of claim 1, wherein the mammal is selected from one of the group consisting of: a human, an ape, a monkey, a mouse, a rat, and a dog.

* * * * *

SEQUENCE LISTING

```
<160> NUMBER OF SEQ ID NOS: 36

<210> SEQ ID NO 1
<211> LENGTH: 23
<212> TYPE: RNA
<213> ORGANISM: Mus musculus

<400> SEQUENCE: 1
uauacauaca cgcacacaua aga                                              23

<210> SEQ ID NO 2
<211> LENGTH: 23
<212> TYPE: DNA
```

```
<213> ORGANISM: Mus musculus

<400> SEQUENCE: 2
tcttatgtgt gcgtgtatgt ata                                          23

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctcttatgtg tgcgtgtatg tata                                         24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(19)
<223> OTHER INFORMATION: May or may not be present

<400> SEQUENCE: 4
tcttatgtgt gcgtgtatgt ata                                          23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: misc_feature
<222> LOCATION: (4)..(4)
<223> OTHER INFORMATION: May or may not be present

<400> SEQUENCE: 5
tcuttatgtg tgcgtgtatg tata                                         24

<210> SEQ ID NO 6
<211> LENGTH: 23
<212> TYPE: RNA
<213> ORGANISM: Homo sapiens

<400> SEQUENCE: 6
ugugcaaauc caugcaaaac uga                                          23

<210> SEQ ID NO 7
<211> LENGTH: 23
<212> TYPE: DNA
<213> ORGANISM: Homo sapiens

<400> SEQUENCE: 7
tcagttttgc atggatttgc aca                                          23

<210> SEQ ID NO 8
<211> LENGTH: 21
```

```
<212> TYPE: RNA
<213> ORGANISM: Mus musculus

<400> SEQUENCE: 8
cugggaagca guggagggga g                                        21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cugggaagca guggagggga gc                                       22

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (19)..(19)
<223> OTHER INFORMATION: May or may not be present

<400> SEQUENCE: 10
cugggaagca guggagggga g                                        21

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (3)..(3)
<223> OTHER INFORMATION: May or may not be present

<400> SEQUENCE: 11
cugcggaagc aguggagggg ag                                       22

<210> SEQ ID NO 12
<211> LENGTH: 24
<212> TYPE: RNA
<213> ORGANISM: Homo sapiens

<400> SEQUENCE: 12
uggcccugac ugaagaccag cagu                                     24

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggctgtattc ccctccg                                             17

<210> SEQ ID NO 14
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagttggta acaatgccat gt                                              22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggattcgac ttagacttga cct                                             23

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcggtgtcat aatgtctctc ag                                              22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagctgcagc tgcccacact g                                               21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gccttgaggg agaagacc                                                   18

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aacagccact cacgcacagt g                                               21

<210> SEQ ID NO 20
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcacaacgaa ctggctgtct g                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aagactatcg acatggagct g                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtaccgcttc tcggagctct g                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctgcattgc acttatgctg a                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaagggcgat ctagtgatgg a                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggtgtgaact gtcaccgatc a                                              21

<210> SEQ ID NO 26
<211> LENGTH: 23
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 26
gtttaggatg tgaacctccc ttg                                           23

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gagaagaact gctgtgtgcg                                               20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gtgtccaggc tccaaatata gg                                            22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
attccagaaa cgccacctcc                                               20

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctattgaac accaaaatgc agg                                           23

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcgtgcggct ctactacatc                                               20

<210> SEQ ID NO 32
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 32
gcacattcgg gtcaactggt a                                              21

<210> SEQ ID NO 33
<211> LENGTH: 23
<212> TYPE: RNA
<213> ORGANISM: Mus musculus

<400> SEQUENCE: 33
guugaccugu uuugauaugu auu                                            23

<210> SEQ ID NO 34
<211> LENGTH: 22
<212> TYPE: RNA
<213> ORGANISM: Mus musculus

<400> SEQUENCE: 34
ugauaaguau auucuaugua ua                                             22

<210> SEQ ID NO 35
<211> LENGTH: 23
<212> TYPE: RNA
<213> ORGANISM: Mus musculus

<400> SEQUENCE: 35
cuccgucgua guauucaugu aug                                            23

<210> SEQ ID NO 36
<211> LENGTH: 23
<212> TYPE: RNA
<213> ORGANISM: Mus musculus

<400> SEQUENCE: 36
uggcaccaca acccugaugu aua                                            23
```